United States Patent
Hölscher

(10) Patent No.: US 9,644,171 B2
(45) Date of Patent: May 9, 2017

(54) CYCLIC ACETALS AND KETALS AND USE THEREOF AS FRAGRANCE

(71) Applicant: Symrise AG, Holzminden (DE)

(72) Inventor: Bernd Hölscher, Halle (DE)

(73) Assignee: Symrise AG, Holzminden (DE)

( * ) Notice: Subject to any disclaimer, the term of this patent is extended or adjusted under 35 U.S.C. 154(b) by 0 days.

(21) Appl. No.: 14/891,848

(22) PCT Filed: Feb. 18, 2014

(86) PCT No.: PCT/EP2014/053121
§ 371 (c)(1),
(2) Date: Nov. 17, 2015

(87) PCT Pub. No.: WO2014/183883
PCT Pub. Date: Nov. 20, 2014

(65) Prior Publication Data
US 2016/0090548 A1    Mar. 31, 2016

(30) Foreign Application Priority Data

May 17, 2013  (EP) .................................... 13168230

(51) Int. Cl.
| | | |
|---|---|---|
| A61K 8/00 | (2006.01) | |
| C11B 9/00 | (2006.01) | |
| A61Q 13/00 | (2006.01) | |
| C07D 317/70 | (2006.01) | |
| C11D 3/50 | (2006.01) | |
| D06M 13/00 | (2006.01) | |
| A61K 8/49 | (2006.01) | |
| A61Q 5/02 | (2006.01) | |
| A61Q 19/10 | (2006.01) | |
| C07D 319/08 | (2006.01) | |

(52) U.S. Cl.
CPC ............ *C11B 9/0076* (2013.01); *A61K 8/498* (2013.01); *A61K 8/4973* (2013.01); *A61Q 5/02* (2013.01); *A61Q 13/00* (2013.01); *A61Q 19/10* (2013.01); *C07D 317/70* (2013.01); *C07D 319/08* (2013.01); *C11B 9/0084* (2013.01); *C11B 9/0088* (2013.01); *C11D 3/50* (2013.01); *D06M 13/005* (2013.01)

(58) Field of Classification Search
CPC ..... C11B 9/0076; C11B 9/008; A61K 8/4973; A61K 8/498
See application file for complete search history.

(56) References Cited

U.S. PATENT DOCUMENTS

2007/0010542 A1    1/2007  Miyazawa et al.

FOREIGN PATENT DOCUMENTS

| DE | 36 03 661 A1 | 8/1987 |
|---|---|---|
| EP | 221 444 A1 | 5/1987 |
| EP | 266 648 A2 | 5/1988 |
| EP | 353 670 A1 | 2/1990 |
| EP | 761 664 A1 | 3/1997 |
| EP | 1 496 055 A1 | 1/2005 |
| EP | 1 679 311 A1 | 7/2006 |
| EP | 2 287 158 A1 | 2/2011 |
| EP | 2 524 959 A1 | 11/2012 |
| GB | 860 498 A | 2/1961 |

OTHER PUBLICATIONS

Xu et al, "Exploitation and application of natural edible fungi as cigarette flavor," XP-002716032 and Database accession No. 147:349982.
Yang et al, "Analysis of flavor components in Yunxiao vinegar by GC-MS," XP-002716033 and Database accession No. 155:681848.
Peters et al, "Synthesis and Conformation of Some 2,4-Dioxa- and 2,4-Dioxa-3-Silabicyclo[3.3.1]Nonanes," Tetrahedron, vol. 38, No. 24, 1982. pp. 3641-3647.
Brown et al, "Acid-Promoted Reaction of Cyclic Allylic Diols with Carbonyl Compounds. Stereoselective Ring-Enlarging Tetrahydrofuran Annulations," J. Am. Chem. Soc 1991. vol. 113, No. 14, pp. 5365-5378.

*Primary Examiner* — John Hardee
(74) *Attorney, Agent, or Firm* — Dilworth & Barrese, LLP

(57) ABSTRACT

The present invention relates to compounds of the formula (I) and use thereof as fragrance. In a further aspect the present invention relates to compositions and fragrance mixtures containing compounds of the formula (I) and the products perfumed with these compositions and fragrance mixtures.

Further, the present invention relates to a method for intensifying an odor or several odors selected from the group consisting of fruity, floral, spicy, woody, musk and ambrette and a method for endowing hair or textile fibers with one, several or all of the notes selected from the group consisting of fruity, floral, spicy, woody, musk and ambrette with use of one or more compounds of the formula (I).

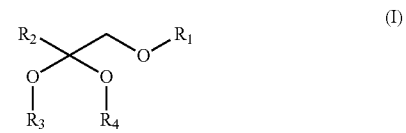

(I)

17 Claims, No Drawings

CYCLIC ACETALS AND KETALS AND USE THEREOF AS FRAGRANCE

In a first aspect the present invention relates to compounds of the formula (I) defined below and in particular use thereof as fragrances. In a further aspect, the present invention relates to compositions and fragrance mixtures containing compounds of the formula (I) defined below and the products perfumed with these compositions and fragrance mixtures.

Further, the present invention relates to a method for intensifying an odor or several odors selected from the group consisting of fruity, floral, spicy, woody, musky and ambrette and a method for endowing hair or textile fibers with one, several or all of the notes selected from the group consisting of fruity, floral, spicy, woody, musk and ambrette with use of one or more compounds of the formula (I) defined below.

Because of the generally insufficient availability of many natural fragrance components, the necessary adaptation to changing fashion trends and the constantly rising demand for new fragrances which alone or in the form of compositions are valuable perfume substances or perfumes with interesting perfume notes, there is an ongoing demand for compounds with interesting fragrance qualities.

Furthermore, because of the rising demand from consumers for novel fragrance notes, there is in the perfume industry a constant demand for fragrances with which novel effects can be achieved in perfumes and with which novel fashion trends can thus be created.

In spite of a large number of already existing fragrances, there is also an ongoing general demand in the perfume industry for novel fragrances, in particular for those which in addition to their primary, namely fragrance, properties, also possess additional positive secondary properties, such as for example higher stability under certain use conditions, high spreading capacity, high radiance, good diffusivity (i.e. good spatial effect), fullness, strength and/or naturalness, odor-intensifying properties or else also better dermatological properties with comparable primary olfactory properties.

There is therefore in the perfume industry essentially a need for further fragrances which are suitable for the production of fragrance compositions or perfumed articles. In particular, there is a need for fragrances which through the above-mentioned technical properties lead to increased use of fragrance compositions and perfume oils.

Cedrane derivatives of the formula (V) are described in EP 857 723 A1 and in EP 2 287158 A1. According to this, compounds of this substance class possess an odor of the ambergris type and simultaneously procure a radiant, strong effect, which intensifies quite diverse perfume notes and prolongs their fragrance effect.

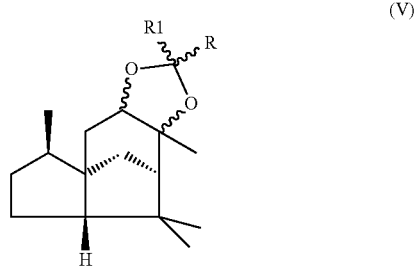

(V)

A commercially available compound of the formula (V) is the compound [(4aR,5R,7aS,9R)-octahydro-2,2,5,8,8,9a-hexamethyl-4H-4a,9-methanoazuleno-(5,6-d)-1,3-dioxole, CAS No. 211299-54-6; hereinafter: Ambrocenide®], which is also described in EP 0 857 723 A1. Its structure corresponds to the following formula (V'):

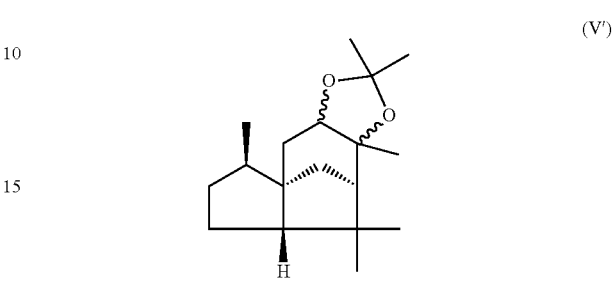

The wavy lines in formula (V') indicate the possible alpha- and beta-configuration of the compound. In other words, Ambrocenide® of the formula (V') can comprise one, two, three or all of the following diastereoisomers:

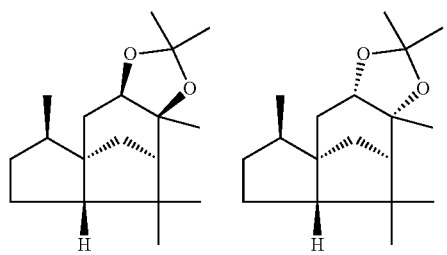

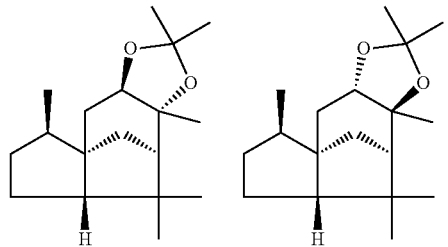

For use of a substance as a fragrance, however, as well as an interesting odor profile, still other properties are also important, such as for example stability, compatibility with other fragrances, solubility and toxicological safety.

Further, other important properties are the adhesive capacity or substantivity of a fragrance, in particular on fibers and/or hair. This property is particularly important for surfactant-containing products such as shampoos, detergents and fabric softeners.

Of particular interest for the perfuming of surfactant-containing formulations are ambergris fragrances with strong intrinsic adhesion. Particularly in demand in this context is the odor note of white ambergris ("white amber"). In perfumery terms, "white amber" is understood to mean the odor of aged natural ambergris, which is a very valuable odor note. Apart from this, the ambergris fragrances should have good biodegradability or bioaccumulation.

A primary objective of the present invention is therefore to provide compounds which fulfil as many as possible of the requirements defined above.

In particular, it is an objective of the present invention to provide a substance (mixture or single compound) with an ambergris odor and especially strong intrinsic adhesion, which preferably has an odor note of white ambergris and in addition has an improved toxicological profile.

These problems are solved according to the invention through compounds of the formula (I)

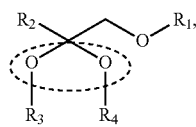
(I)

wherein $R_1$ is or are hydrogen or $C_1$-$C_3$ alkyl, preferably hydrogen, methyl or ethyl, and $R_2$ hydrogen or $C_1$-$C_4$ alkyl, preferably hydrogen, methyl or ethyl, preferably wherein $R_1$ and/or $R_2$ is or are methyl or $R_1$ methyl and $R_2$ hydrogen, and $R_3$ and $R_4$ together with the dioxolane unit (as circled or marked above by the dotted line) form a 5-8 membered ring (i.e. a ring which contains the two oxygen atoms, the carbon atom linking the two oxygen atoms and the "residues" $R_3$ and $R_4$; see below for preferred meanings and formulae), wherein the ring optionally contains a double bond, and wherein the ring is optionally substituted with one or more branched or unbranched, bridged or unbridged alkyl groups, alkenyl groups, cycloalkyl groups, cycloalkenyl groups, aryl groups, arylalkyl groups, alkoxyalkyl groups or alkoxyaryl groups, and $R_3$ and $R_4$ in total contain 3 to 16 carbon atoms.

Preferably, $R_3$ and $R_4$ together with the dioxolane unit form a 5- or 6-membered ring (concerning this, see below, compounds of the formulae (II), (In, (Ill) and (IV) or (IV')).

All stereoisomers which arise through asymmetrical substitution of the central carbon atom are comprised by the aforesaid formula (I). In other words, the compounds of the formula (I) described herein can in each case be present in the form of a specific stereoisomer or in the form of any mixture of different stereoisomers.

According to one preferred aspect of the present invention, a compound of the formula (I) contains in total 15 carbon atoms.

Particularly suitable according to the invention are compounds of the formula (II) or (II')

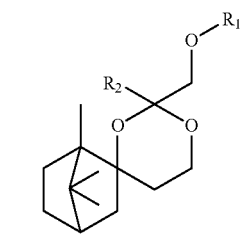
(II)

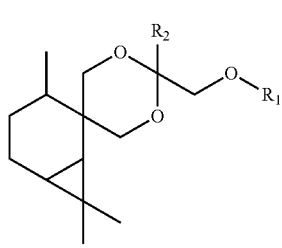
(II')

wherein $R_1$ is or are hydrogen or $C_1$-$C_3$ alkyl, preferably hydrogen, methyl or ethyl, and $R_2$ hydrogen or $C_1$-$C_4$ alkyl, preferably hydrogen, methyl or ethyl, preferably wherein $R_1$ and/or $R_2$ is or are methyl or $R_1$ methyl and $R_2$ hydrogen.

All stereoisomers which arise through asymmetrical substitution of the central carbon atom are comprised by the aforesaid formula (II). In other words, the compounds of the formula (II) described herein can in each case be present in the form of a specific stereoisomer or in the form of any mixture of different stereoisomers.

Also particularly suitable are compounds of the formula (III)

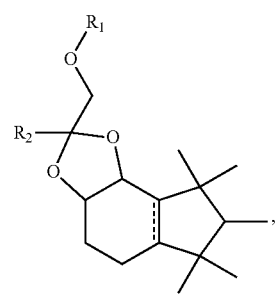
(III)

wherein $R_1$ is or are hydrogen or $C_1$-$C_3$ alkyl, preferably hydrogen, methyl or ethyl, and $R_2$ hydrogen or $C_1$-$C_4$ alkyl, preferably hydrogen, methyl or ethyl, preferably wherein $R_1$ and/or $R_2$ is or are methyl or $R_1$ methyl and $R_2$ hydrogen, and the compound is saturated or unsaturated.

In the formula (III) stated above, the dotted line indicates that the compound can be saturated or unsaturated. If the compound is saturated, the five- and six-membered ring are joined by a shared single bond; if the compound is unsaturated, the five- and six-membered ring are joined by a shared double bond.

Quite especially suitable and therefore preferred according to the invention are compounds of the formula (IV) or (IV')

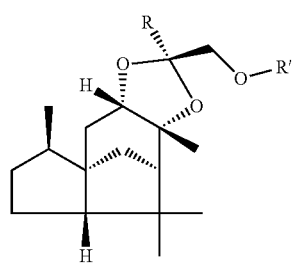
(IV)

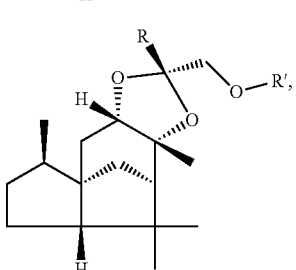
(IV')

wherein: R═H or $C_1$-$C_4$ alkyl and R'═H or $C_1$-$C_3$ alkyl, preferably R═R'═$C_1$ alkyl (moreover, for preferred residues the aforesaid applies as appropriate).

In particular the stereoisomer of the formula (IV) is characterized by a strong odor of ambergris and wood and advantageously possesses better biodegradability or better bioaccumulation compared to compounds named in EP 857 723 A1 and EP 2 287158 A1. In general, it should be noted at this point that all of the advantages of compounds according to the invention mentioned herein essentially applies for the totality of the compounds according to the invention described herein, but quite especially for the compounds designated herein as preferred.

In the olfactory evaluation of compounds according to the invention (as described herein) these, in particular those as described above as preferred, proved of interest not only in odor terms. It was further found that these compounds have unusually long adhesion, which even exceeds that of Ambrocenide® (EP 857 723 A1).

The compounds according to the invention of the formulae VIII and IX can for example be prepared by reaction of cis-cedranediol (compound of the formula (VI) which is preparable from α-cedrene) with 1-methoxy-propan-2-one (compound of the formula (VII)).

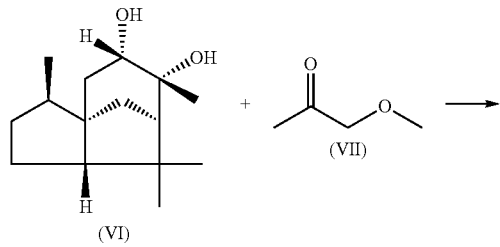

(VI)

(VII)

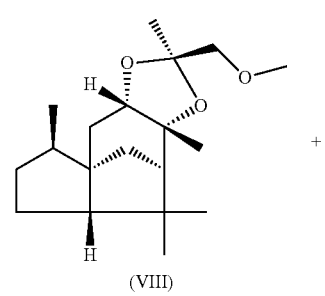

(VIII)

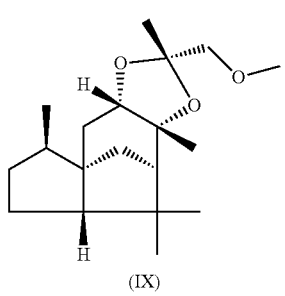

(IX)

Analogously, by reaction of cis-cedranediol with methoxyacetaldehyde dimethyl acetal, the compounds according to the invention of the formulae (X) and (XI) can be obtained.

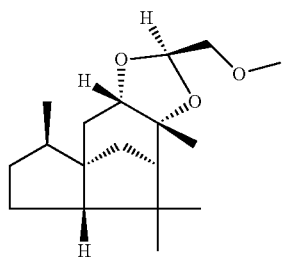

(X)

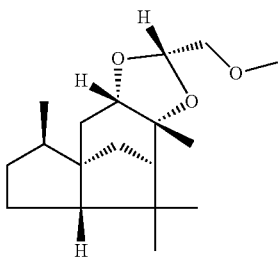

(XI)

Preferably, the compounds according to the invention of the formulae VIII and IX or X and XI respectively are prepared by reaction of cis-cedranediol (formula VI) with 1-methoxy-propan-2-one or methoxyacetaldehyde dimethyl acetal in presence of one or more water-binding substances and one or more acids.

Accordingly, the present invention also relates to corresponding production processes (as described above). In particular the present invention relates to a method for the production of compounds particularly preferred according to the invention of the formula (I) (see above, compounds of the formulae (VIII) to (XI)) with the following step: reaction of a compound of the formula (VI) (as shown above) with a compound of the formula (VII) (as shown above) or with methoxyacetaldehyde dimethyl acetal, preferably in presence of one or more water-binding substances and one or more acids. Further compounds according to the invention (as described herein) can also be produced in a corresponding manner.

Preferred water-binding substances are selected from the group consisting of orthoformate esters (preferably trimethyl orthoformate or triethyl orthoformate) and 2,2-dialkoxypentanes (preferably 2,2-dimethoxypentane or 2,2-diethoxy-pentane).

The acids optionally used are preferably selected from the group consisting of inorganic protic acids, organic protic acids and acidic fixed bed catalysts.

Preferably, the reaction of cis-cedranediol (formula (VI)) with 1-methoxy-propan-2-one or methoxyacetaldehyde dimethyl acetal to give the compounds according to the invention of the formulae VIII and IX or X and XI respectively takes place at a reaction temperature in the range from 0 to 70° C.

The compounds of the formulae (VIII) to (XI) are particularly preferred for the purposes of the invention described herein.

A further aspect of the present invention relates to compositions comprising or consisting of
(i) one or more 3,6,8,8-tetramethyl-octahydro-3a,7-methano-azulen-5,6-diol ketal(s) and
(ii) one or more compound(s) of the formula (I), preferably one or more compound(s) of the formula (IV) and one or more compound(s) of the formula (IV'), characterized in that
the total content of the compounds of the formula (I) or of the compounds of the formulae (IV) and (IV') is greater than 40 wt. %, preferably greater than 55 wt. %, preferably greater than 70 wt. %, more preferably greater than 85 wt. %, and especially preferably greater than 95 wt. %, based on the total quantity of the 3,6,8,8-tetramethyl-octahydro-3a,7-methano-azulen-5,6-diol ketals contained in the composition,
and/or that
the weight ratio of the compound(s) of the formula (IV) to the compound(s) of the formula (IV'), if present, lies in the range from 4:1 to 1:10, preferably in the range from 2:1 to 1:6, and especially preferably in the range from 1:1 to 1:3.

For compounds of the formula (I) preferably to be selected here, the aforesaid applies as appropriate.

The compounds according to the invention of the formula (I) are advantageously characterized by high absorbability (i.e. intrinsic adhesion on a substrate) and high substantivity (i.e. ability to absorb onto a substrate out of a, mostly aqueous, phase, or to remain on a substrate even after a washing or rinsing procedure). This effect is in particular seen on substrates such as skin, hair and textile fibers (e.g. wool, cotton, linen, synthetic fibers). The terms "substantivity" and "retention" are comprehensively described for example in EP 1 201 738 A1 (compare there the paragraphs [0004]-[0005]).

Corresponding to this knowledge, a further aspect of the present invention relates to the use of the compounds according to the invention or a composition according to the invention (as described above) as a means for increasing the substantivity and/or retention of a fragrance mixture (in particular towards or on hair or textile fibers), preferably a fragrance mixture with fruity, floral and/or spicy notes.

As well as their high absorbability, the compounds according to the invention of the formula (I) are also characterized by their fixing properties, i.e. they advantageously function as a fixative. As fixatives, the compounds according to the invention increase the adhesive strength of other fragrances, whether this is due to a decrease in their vapor pressure or olfactory intensification (e.g. lowering of the threshold value).

A further aspect of the present invention therefore also relates to the use of the compounds according to the invention (as described above) or a composition according to the invention (as described above) as fixatives.

Also a subject of the present invention therefore is the use of a compound according to the invention (as described above) or a composition according to the invention (as described above) as a
fragrance or fragrance mixture, preferably as a fragrance or fragrance mixture with the perfume notes ambergris and/or wood,
means for increasing the substantivity and/or the retention of a fragrance mixture, or
fixative.

A further subject of the present invention are fragrance mixtures, preferably perfume oils, comprising or consisting of
one or more compound(s) of the formula (I), preferably of the formula (IV), or a composition according to the invention
and
one or more (further) fragrance(s) not corresponding to the formula (I), characterized in that
(i) the quantity of the compound(s) of the formula (I), preferably of the formula (IV), suffices to procure an ambergris note and/or wood note, in particular a white ambergris note ("white amber"),
and/or that
(ii) the (further) fragrance(s) not corresponding to the formula (I) procure one, several or all of the notes fruity, floral, spicy, woody, musk and ambrette and the quantity of the compound(s) of the formula (I), preferably of the formula (IV), suffices to modify and/or to intensify one, several or all of the notes fruity, floral, spicy, woody, musk and ambrette,
and/or that
(iii) the quantity of the compound(s) of the formula (I), preferably of the formula (IV), suffices to impart to the fragrance mixture an impression of volume, complexity, elegance and/or naturalness,
and/or that
(iv) the quantity of the compound(s) of the formula (I), preferably of the formula (IV), suffices, in comparison to an otherwise identically constituted fragrance mixture without compounds of the formula (I), to create a more nurturing, more harmonious, higher quality and/or more natural olfactory impression.

For compounds of the formula (I) preferably to be selected here, the aforesaid applies as appropriate.

A preferred fragrance mixture or a preferred perfume oil is characterized in that the quantity of the compound(s) of the formula (I), preferably of the formula (IV), lies in the range from 0.0001 to 25 wt. %, preferably in the range from 0.001 to 15 wt. %, based on the total weight of the fragrance mixture.

Fragrance mixtures according to the invention, in particular perfume oils, preferably comprise two, three, four, five, six, seven, eight, nine, ten or more fragrances, preferably selected from the substances mentioned below:

Fragrances which are mentioned in Steffen Arctander, Perfume and Flavor Chemicals, published by author, Montclair, N. J. 1969; H. Surburg, J. Panten, Common Fragrance and Flavor Materials, 5th Edition, Wiley-VCH, Weinheim 2006.

As fragrances or fragrance-containing substances preferably combinable with the compounds and compositions according to the invention, the following may in particular be mentioned:

Extracts from natural raw materials such as essential oils, concretes, absolutes, resins, resinoids, balsams and tinctures such as for example ambergris tincture, amyris oil, *angelica* seed oil, *angelica* root oil, anise oil, valerian oil, basil oil, treemoss absolute, bay oil, mugwort oil, benzoin resin, bergamot oil, beeswax absolute, birch tar oil, bitter almond oil, summer savory, buchu oil, cabreuva oil, cade oil, calamus oil, camphor oil, *cananga* oil, cardamom oil, cascarilla oil, *cassia* oil, *cassia* absolute, castoreum absolute, cedar leaf oil, cedarwood oil, cistus oil, citronella oil, lemon oil, copaiva balsam, copaiva balsam oil, coriander oil, costus root oil, cumin oil, cypress oil, davana oil, dillweed oil, dillseed oil, eau de brouts absolute, oakmoss absolute, elemi oil, tarragon oil, *eucalyptus citriodora* oil, *eucalyptus* oil, fennel oil, spruce needle oil, *galbanum* oil, *galbanum* resin, geranium oil, grapefruit oil, guaiac wood oil, gurjun balsam, gurjun balsam oil, helichrysum absolute, helichrysum oil, ginger oil, iris root absolute, iris root oil, jasmine absolute, calamus oil, chamomile oil blue, chamomile oil Roman, carrot seed oil, cascarilla oil, dwarf pine needle oil, spearmint oil, caraway oil, labdanum oil, labdanum absolute, labdanum resin, lavandin absolute, lavandin oil, lavender absolute, lavender oil, lemongrass oil, lovage oil, sweet lime oil distilled, sweet lime oil pressed, linaloa oil, *litsea cubeba* oil, laurel leaf oil, mace oil, marjoram oil, mandarin oil, *massoia* bark oil, *mimosa* absolute, ambrette seed oil, ambrette tincture, clary sage oil, nutmeg oil, myrrh absolute, myrrh oil, myrtle oil, clove leaf oil, clove flower oil, neroli oil, olibanum absolute, olibanum oil, opopanax oil, orange flower absolute, orange oil, oregano oil, palmarosa oil, patchouli oil, *perilla* oil, Peru balsam oil, parsley leaf oil, parsley seed oil, petitgrain oil, peppermint oil, pepper oil, pimento oil, pine oil, pennyroyal oil, rose absolute, rosewood oil, rose oil, rosemary oil, sage oil Dalmatian, sage oil Spanish, sandalwood oil, celery seed oil, spike lavender oil, star anise oil, *styrax* oil, *tagetes* oil, fir needle oil, tea tree oil, turpentine oil, thyme oil, tolu balsam, tonka absolute, tuberose absolute, vanilla extract, violet leaf absolute, *verbena* oil, vetiver oil, juniper oil, wine yeast oil, wormwood oil, wintergreen oil, ylang-ylang oil, hyssop oil, civet absolute, cinnamon leaf oil, cinnamon bark oil, and fractions therefrom or components isolated therefrom;

individual fragrances from the group of the hydrocarbons, such as for example 3-carene, α-pinene, β-pinene, α-terpinene, γ-terpinene, p-cymene, bisabolene, camphene, caryophyllene, cedrene, farnesene, limonene, longifolene, myrcene, ocimene, valencene, and (E,Z)-1,3,5-undecatriene, from the group of the aliphatic alcohols, such as for example hexanol, octanol, 3-octanol, 2,6-dimethylheptanol, 2-methylheptanol, 2-methyloctanol, (E)-2-hexenol, (E)- and (Z)-3-hexenol, 1-octen-3-ol, mixture of 3,4,5,6,6-pentamethyl-3/4-hepten-2-ol and 3,5,6,6-tetramethyl-4-methyleneheptan-2-ol, (E,Z)-2,6-nonadienol, 3,7-dimethyl-7-methoxyoctan-2-ol, 9-decenol, 10-undecenol and 4-methyl-3-decen-5-ol, from the group of the aliphatic aldehydes and acetals thereof such as for example hexanal, heptanal, octanal, nonanal, decanal, undecanal, dodecanal, tridecanal, 2-methyloctanal, 2-methylnonanal, (E)-2-hexenal, (Z)-4-heptenal, 2,6-dimethyl-5-heptenal, 10-undecenal, (E)-4-decenal, 2-dodecenal, 2,6,10-trimethyl-5,9-undecadienal, heptanal diethyl acetal, 1,1-dimethoxy-2,2,5-trimethyl-4-hexene and citronellyloxyacetaldehyde;

from the group of the aliphatic ketones and oximes thereof such as for example 2-heptanone, 2-octanone, 3-octanone, 2-nonanone, 5-methyl-3-heptanone, 5-methyl-3-heptanone oxime and 2,4,4,7-tetramethyl-6-octen-3-one;

from the group of the aliphatic sulfur-containing compounds such as for example 3-methylthiohexanol, 3-methylthiohexyl acetate, 3-mercaptohexanol, 3-mercaptohexyl acetate, 3-mercaptohexyl butyrate, 3-acetylthiohexyl acetate and 1-menthen-8-thiol, from the group of the aliphatic nitriles such as for example 2-nonenonitrile, 2-tridecenonitrile, 2,12-tridecenonitrile, 3,7-dimethyl-2,6-octadienonitrile and 3,7-dimethyl-6-octenonitrile, from the group of the aliphatic carboxylic acids and esters thereof such as for example (E)- and (Z)-3-hexenyl formate, ethyl acetoacetate, isoamyl acetate, hexyl acetate, 3,5,5-trimethylhexyl acetate, 3-methyl-2-butenyl acetate, (E)-2-hexenyl acetate, (E)- and (Z)-3-hexenyl acetate, octyl acetate, 3-octyl acetate, 1-octen-3-yl acetate, ethyl butyrate, butyl butyrate, isoamyl butyrate, hexyl butyrate, (E)- and (Z)-3-hexenyl isobutyrate, hexyl crotonate, ethyl isovalerate, ethyl 2-methyl pentanoate, ethyl hexanoate, allyl hexanoate, ethyl heptanoate, allyl heptanoate, ethyl octanoate, ethyl (E,Z)-2,4-decadienoate, methyl 2-octynate, methyl 2-nonynate, allyl 2-isoamyloxyacetate and methyl 3,7-dimethyl-2,6-octadienoate;

from the group of the acyclic terpene alcohols such as for example citronellol, geraniol, nerol, linalool, lavandulol, nerolidol, farnesol, tetrahydrolinalool, tetrahydrogeraniol, 2,6-dimethyl-7-octen-2-ol, 2,6-dimethyloctan-2-ol, 2-methyl-6-methylen-7-octen-2-ol, 2,6-dimethyl-5,7-octadien-2-ol, 2,6-dimethyl-3,5-octadien-2-ol, 3,7-dimethyl-4,6-octadien-3-ol, 3,7-dimethyl-1,5,7-octatrien-3-ol, 2,6-dimethyl-2,5,7-octatrien-1-ol, and formates, acetates, propionates, isobutyrates, butyrates, isovalerates, pentanoates, hexanoates, crotonates, tiglates and 3-methyl-2-butenoates thereof, from the group of the acyclic terpene aldehydes and ketones such as for example geranial, neral, citronellal, 7-hydroxy-3,7-dimethyloctanal, 7-methoxy-3,7-dimethyloctanal, 2,6,10-trimethyl-9-undecenal and geranylacetone, and the dimethyl and diethyl acetals of geranial, neral and 7-hydroxy-3,7-dimethyloctanal, from the group of the cyclic terpene alcohols such as for example menthol, isopulegol, α-terpineol, terpinenol-4, menthan-8-ol, menthan-1-ol, menthan-7-ol, borneol, isoborneol, linalool oxide, nopol, cedrol, ambrinol, vetiverol, guaiol, and formates, acetates, propionates, isobutyrates, butyrates, isovalerates, pentanoates, hexanoates, crotonates, tiglates and 3-methyl-2-butenoates thereof;

from the group of the cyclic terpene aldehydes and ketones such as for example menthone, isomenthone, 8-mercaptomenthan-3-one, carvone, camphor, fenchone, α-ionone, β-ionone, α-n-methylionone, β-n-methylionone, α-isomethylionone, β-isomethylionone, α-irone, α-damascone, β-damascone, β-damascenone, γ-damascone, δ-damascone, 1-(2,4,4-trimethyl-2-cyclohexen-1-yl)-2-buten-1-one, 1,3,4,6,7,8a-hexahydro-1,1,5,5-tetramethyl-2H-2,4a-methanonaphthalen-8(5H)-one, nootkatone, dihydronootkatone, α-sinensal, β-sinensal and acetylated cedarwood oil (methyl cedryl ketone);

from the group of the cyclic alcohols such as for example 4-tert-butylcyclohexanol, 3,3,5-trimethylcyclohexanol, 3-isocamphylcyclohexanol, 2,6,9-trimethyl-(Z2,Z5,E9)-cyclododecatrien-1-ol and 2-isobutyl-4-methyl-tetrahydro-2H-pyran-4-ol;

from the group of the cycloaliphatic alcohols such as for example α,3,3-trimethylcyclohexylmethanol, 2-methyl-4-(2,2,3-trimethyl-3-cyclopent-1-yl)-butanol, 2-methyl-4-(2,2,3-trimethyl-3-cyclopent-1-yl)-2-buten-1-ol, 2-ethyl-4-(2,2,3-trimethyl-3-cyclopent-1-yl)-2-buten-1-ol, 3-methyl-5-(2,2,3-trimethyl-3-cyclopent-1-yl)-pentan-2-ol, 3-methyl-5-(2,2,3-tri methyl-3-cyclopent-1-yl)-4-penten-2-ol, 3,3-dimethyl-5-(2,2,3-trimethyl-3-cyclopent-1-yl)-4-penten-2-ol, 1-(2,2,6-trimethylcyclohexyl)pentan-3-ol and 1-(2,2,6-trimethylcyclohenrhhexan-3-ol;

from the group of the cyclic and cycloaliphatic ethers such as for example cineole, cedryl methyl ether, cyclododecyl methyl ether, (ethoxymethoxy)-cyclododecane, α-cedrene epoxide, 3a,6,6,9a-tetramethyldodecahydro-naphtho[2,1-b]furan, 3a-ethyl-6,6,9a-tri methyldodecahydronaphtho[2,1-b]furan, 1,5,9-trimethyl-13-oxabicyclo[10.1.0]trideca-4,8-diene, rose oxide and 2-(2,4-dimethyl-3-cyclohexen-1-yl)-5-methyl-5-(1-methylpropyl)-1,3-dioxan;

from the group of the cyclic ketones such as for example 4-tert-butylcyclo-hexanone, 2,2,5-trimethyl-5-pentylcyclopentanone, 2-heptylcyclopentanone, 2-pentylcyclopentanone, 2-hydroxy-3-methyl-2-cyclopenten-1-one, 3-methyl-cis-2-penten-1-yl-2-cyclopenten-1-one, 3-methyl-2-pentyl-2-cyclopenten-1-one, 3-methyl-4-cyclopentadecenone, 3-methyl-5-cyclopentadecenone, 3-methyl-cyclopentadecanone, 4-(1-ethoxyvinyl)-3,3,5,5-tetramethylcyclohexanone, 4-tert-pentylcyclohexanone, 5-cyclohexadecen- 1-one, 6,7-dihydro-1,1,2,3,3-pentamethyl-4(5H)-indanone, 9-cycloheptadecen-1-one, cyclopenta-decanone and cyclohexadecanone;

from the group of the cycloaliphatic aldehydes such as for example 2,4-dimethyl-3-cyclohexencarbaldehyde, 2-methyl-4-(2,2,6-trimethyl-cyclohexen-1-yl)-2-butenal, 4-(4-hydroxy-4-methylpentyl)-3-cyclohexencarbaldehyde and 4-(4-methyl-3-penten-1-yl)-3-cyclohexencarbaldehyde;

from the group of the cycloaliphatic ketones such as for example 1-(3,3-dimethylcyclohexyl)-4-penten-1-one, 1-(5,5-dimethyl-1-cyclohexen-1-yl)-4-penten-1-one, 2,3,8,8-tetramethyl-1,2,3,4,5,6,7,8-octahydro-2-naphthalenyl methyl ketone, methyl 2,6,10-trimethyl-2,5,9-cyclododecatrienyl ketone and tert-butyl (2,4-dimethyl-3-cyclohexen-1-yl) ketone;

from the group of the esters of cyclic alcohols such as for example 2-tert-butylcyclohexyl acetate, 4-tert-butylcyclohexyl acetate, 2-tert-pentylcyclohexyl acetate, 4-tert-pentylcyclohexyl acetate, decahydro-2-naphthyl acetate, 3-pentyltetrahydro-2H-pyran-4-yl acetate, decahydro-2,5,5,8a-tetramethyl-2-naphthyl acetate, 4,7-methano-3a,4,5,6,7,7a-hexahydro-5- or -6-indenyl acetate, 4,7-methano-3a,4,5,6,7,7a-hexahydro-5- or -6-indenyl propionate, 4,7-methano-3a,4,5,6,7,7a-hexahydro-5- or -6-indenyl isobutyrate and 4,7-methanooctahydro-5- or -6-indenyl acetate;

from the group of the esters of cycloaliphatic carboxylic acids such as for example allyl 3-cyclohexylpropionate, allyl cyclohexyloxyacetate, methyl dihydrojasmonate, methyl jasmonate, methyl 2-hexyl-3-oxocyclopentane-carboxylate, ethyl 2-ethyl-6,6-dimethyl-2-cyclohexenecarboxylate, ethyl 2,3,6,6-tetramethyl-2-cyclohexenecarboxylate and ethyl 2-methyl-1,3-dioxolan-2-acetate;

from the group of the aromatic hydrocarbons such as for example styrene and diphenylmethane;

from the group of the araliphatic alcohols such as for example benzyl alcohol, 1-phenylethyl alcohol, 2-phenylethyl alcohol, 3-phenylpropanol, 2-phenylpropanol, 2-phenoxyethanol, 2,2-dimethyl-3-phenylpropanol, 2,2-dimethyl-3-(3-methylphenyl)propanol, 1,1-dimethyl-2-phenylethyl alcohol, 1,1-dimethyl-3-phenylpropanol, 1-ethyl-1-methyl-3-phenylpropanol, 2-methyl-5-phenylpentanol, 3-methyl-5-phenylpentanol, 3-phenyl-2-propen-1-ol, 4-methoxybenzyl alcohol and 1-(4-isopropylphenyl)ethanol;

from the group of the esters of araliphatic alcohols and aliphatic carboxylic acids such as for example benzyl acetate, benzyl propionate, benzyl isobutyrate, benzyl isovalerate, 2-phenylethyl acetate, 2-phenylethyl propionate, 2-phenylethyl isobutyrate, 2-phenylethyl isovalerate, 1-phenylethyl acetate, α-trichloromethylbenzyl acetate, α,α-dimethylphenylethyl acetate, α,α-dimethylphenylethyl butyrate, cinnamyl acetate, 2-phenoxyethyl isobutyrate and 4-methoxybenzyl acetate;

from the group of the araliphatic ethers such as for example 2-phenylethyl methyl ether; 2-phenylethyl isoamyl ether; 2-phenylethyl 1-ethoxyethyl ether; phenylacetaldehyde dimethyl acetal; phenylacetaldehyde diethyl acetal; hydratropic aldehyde dimethyl acetal, phenylacetaldehyde glycerin acetal, 2,4,6-trimethyl-4-phenyl-1,3-dioxan, 4,4a,5,9b-tetrahydroindeno[1,2-d]-m-dioxin and 4,4a,5,9b-tetrahydro-2,4-dimethylindeno[1,2-d]m-dioxin;

from the group of the aromatic and araliphatic aldehydes such as for example benzaldehyde, phenylacetaldehyde, 3-phenylpropanal, hydratropic aldehyde, 4-methylbenzaldehyde, 4-methylphenylacetaldehyde, 3-(4-ethylphenyl)-2,2-dimethylpropanal, 2-methyl-3-(4-isopropylphenyl)propanal, 2-methyl-3-(4-tert-butylphenyl)propanal, 3-(4-tert-butylphenyl)propanal, cinnamaldehyde, α-butylcinnamaldehyde, α-amylcinnamaldehyde, α-hexylcinnamaldehyde, 3-methyl-5-phenylpentanal, 4-methoxybenzaldehyde, 4-hydroxy-3-methoxybenzaldehyde, 4-hydroxy-3-ethoxybenzaldehyde, 3,4-methylendioxybenzaldehyde, 3,4-di-methoxybenzaldehyde, 2-methyl-3-(4-methoxyphenyl)propanal and 2-methyl-3-(4-methylendioxyphenyl)propanal;

from the group of the aromatic and araliphatic ketones such as for example acetophenone, 4-methylacetophenone, 4-methoxyacetophenone, 4-tert-butyl-2,6-dimethylacetophenone, 4-phenyl-2-butanone, 4-(4-hydroxyphenyl)-2-butanone, 1-(2-Naphthalenyl)ethanone, benzophenone, 1,1,2,3,3,6-hexamethyl-5-indanyl methyl ketone, 6-tert-butyl-1,1-dimethyl-4-indanyl methyl ketone, 1-[2,3-dihydro-1,1,2,6-tetramethyl-3-(1-methylethyl)-1H-5-indenyl]-ethanone and 5',6',7',8'-tetrahydro-3',5',5',6',8',8'-hexamethyl-2-acetonaphthone;

from the group of the aromatic and araliphatic carboxylic acids and esters thereof such as for example benzoic acid, phenylacetic acid, methyl benzoate, ethyl benzoate, hexyl benzoate, benzyl benzoate, methylphenyl acetate, ethylphenyl acetate, geranylphenyl acetate, phenylethyl phenylacetate, methyl cinnamate, ethyl cinnamate, benzyl cinnamate, phenylethyl cinnamate, cinnamyl cinnamate, allyl phenoxyacetate, methyl salicylate, isoamyl salicylate, hexyl salicylate, cyclohexyl salicylate, cis-3-hexenyl salicylate, benzyl salicylate, phenylethyl salicylate, methyl 2,4-dihydroxy-3,6-dimethylbenzoate, ethyl 3-phenylglycidate and ethyl 3-methyl-3-phenylglycidate;

from the group of the nitrogen-containing aromatic compounds such as for example 2,4,6-trinitro-1,3-dimethyl-5-tert-butylbenzene, 3,5-dinitro-2,6-dimethyl-4-tert-butylacetophenone, cinnamonitrile, 5-phenyl-3-methyl-2-pentenonitrile, 5-phenyl-3-methylpentanonitrile, methyl anthranilate, methyl N-methyl anthranilate, Schiff's bases of methyl anthranilate with 7-hydroxy-3,7-dimethyloctanal, 2-methyl-3-(4-tert-butylphenyl)propanal or 2,4-dimethyl-3-cyclohexencarbaldehyde, 6-isopropylquinoline, 6-isobutylquinoline, 6-sec-butylquinoline, indole, skatole, 2-methoxy-3-isopropylpyrazine, 2-isobutyl-3-methoxypyrazine and 4-(4,8-dimethyl-3,7-nonadienyl)-pyridine;

from the group of the phenols, phenyl ethers and phenyl esters such as for example estragole, anethole, eugenol, eugenyl methyl ether, isoeugenol, isoeugenyl methyl ether, thymol, carvacrol, diphenyl ether, β-naphthyl methyl ether, β-naphthyl ethyl ether, β-naphthyl isobutyl ether, 1,4-dimethoxybenzene, eugenyl acetate, 2-methoxy-4-methylphenol, 2-ethoxy-5-(1-propenyl)phenol and p-cresylphenyl acetate;

from the group of the heterocyclic compounds such as for example 2,5-dimethyl-4-hydroxy-2H-furan-3-one, 2-ethyl-4-hydroxy-5-methyl-2H-furan-3-one, 3-hydroxy-2-methyl-4H-pyran-4-one and 2-ethyl-3-hydroxy-4H-pyran-4-one;

from the group of the lactones such as for example 1,4-octanolide, 3-methyl-1,4-octanolide, 1,4-nonanolide, 1,4-decanolide, 8-decen-1,4-olide, 1,4-undecanolide, 1,4-dodecanolide, 1,5-decanolide, 1,5-dodecanolide, 1,15-pentadecanolide, cis- and trans-11-pentadecen-1,15-olide, cis- and trans-12-pentadecen-1,15-olide, 1,16-hexadecanolide, 9-hexadecen-1,16-olide, 10-oxa-1,16-hexadecanolide, 11-oxa-1,16-hexadecanolide, 12-oxa-1,16-hexadecanolide, ethylene 1,12-dodecanedioate, ethylene 1,13-tridecanedioate, coumarin, 2,3-dihydrocoumarin and octahydrocoumarin.

The compounds according to the invention or a composition according to the invention (as described above) influence the sensory properties of fragrance mixtures in a variety of ways (concerning this, see also the comparative examples below).

A preferred fragrance mixture according to the invention or a preferred perfume oil according to the invention is characterized in that the fragrance mixture or the perfume oil
(i) (additionally) contains one or more wood and/or ambergris fragrance(s) not corresponding to the formula (I) and/or
(ii) one or more musk fragrance(s).

The musk fragrance or fragrances of the component (ii) are fragrances which have a musk odor. Such fragrances are known to those skilled in the art, since "musk" is an important odor descriptor in perfumery.

It is preferred according to the invention that the musk fragrance(s) is/are selected from the group consisting of polycyclic and macrocyclic musk fragrances, preferably from the group consisting of macrocyclic $C_{14}$-$C_{18}$ ketones and macrocyclic $C_{14}$-$C_{18}$ lactones.

Musk fragrances advantageously used in the context of the present invention are listed in Table 1.

Furthermore, it is preferred according to the invention that the weight ratio of musk fragrances to the compound(s) of the formula (I), preferably of the formula (IV), is equal to or greater than 10:1, and preferably lies in the range from 10:1 to 100,000:1, more preferably in the range from 50:1 to 100,000:1, and especially preferably in the range from 100:1 to 100,000:1.

Especially preferable are fragrance mixtures according to the invention which contain 3-methylcyclopentadecenone (Muscenone), 15-pentadec-(11/12)-enolide (Globalide)®, ethylene brassylate, oxacyclohexadecan-2-one (Macrolides), cyclohexadecanone (Isomuscone®), 8-cyclohexadecanone (Globanone®), (7/8)-cyclohexadecanone (Aurelione®) and/or mixtures thereof.

As already mentioned, because of their olfactory properties, the compounds according to the invention are especially suitable for use in fragrance mixtures and in particular perfume oils. For this, the compounds can be used alone or in mixtures in appropriate fragrance mixtures together with

TABLE 1

| TYPE | Product/Brand name | Name/CAS Name |
| --- | --- | --- |
| MACRO | EXALTENONE | 4-cyclopentadecen-1-one (4Z)-; 4-cyclopentadecen-1-one |
| MACRO | CIVETONE | 9-cycloheptadecen-1-one, (9Z)- |
| MACRO | CYCLOHEXADECANOLIDE, DIHYDROAMBRETTOLIDE | Oxacycloheptadecan-2-one, ω-hexadecanolide |
| MACRO | ETHYLENE DODECANEDIOATE | 1,4-dioxacyclohexadecane-5,16-dione |
| MACRO | GLOBALIDE ® | Oxacyclohexadecen-2-one, 15-pentadec-(11/12)-enolide |
| MACRO | ETHYLENE BRASSYLATE | 1,4-dioxacycloheptadecane-5,17-dione |
| MACRO | MUSCONE | 3-methyl-cyclopentadecanone |
| MACRO | AMBRETTOLIDE | Oxacycloheptadec-10-en-2-one |
| MACRO | MUSCENONE | 3-methyl-cyclopentadecenone |
| MACRO | VELVIONE ®, AMBRETONE | 5-cyclohexadecen-1-one |
| MACRO | AURELIONE ® | 7/8-cyclohexadecen-1-one |
| MACRO | GLOBANONE ® | 8-cyclohexadecen-1-one |
| MACRO | ISOMUSCONE ® | Cyclohexadecanone |
| MACRO | EXALTOLIDE, MACROLIDE ® | Oxacyclohexadecan-2-one |
| MACRO | COSMONE ® | 3-methyl-(5E/Z)-cyclotetradecen-1-one |
| POLY | TRASEOLIDE ® | 1-[2,3-dihydro-1,1,2,6-tetramethyl-3-(1-methylethyl)-1H-inden-5-yl]-ethanone |
| POLY | PHANTOLIDE ® | 1-(2,3-dihydro-1,1,2,3,3,6-hexamethyl-1H-inden-5-yl)-ethanone |
| POLY | TONALIDE ® | 1-(5,6,7,8-tetrahydro-3,5,5,6,8,8-hexamethyl-2-naphthalenyl)-ethanone |
| POLY | CRYSOLIDE | 1-[6-(1,1-dimethylethyl)-2,3-dihydro-1,1-dimethyl-1H-inden-4-yl]-ethanone |
| POLY | CHROMANOLIDE ® | 1-methylethyl tetradecanoate; cyclopenta[g]-2-benzopyran, 1,3,4,6,7,8-hexahydro-4,6,6,7,8,8-hexamethyl- |
| POLY | GALAXOLIDE ® | Cyclopenta[g]-2-benzopyran, 1,3,4,6,7,8-hexahydro-4,6,6,7,8,8-hexamethyl- |
| ALICYC | HELVETOLIDE ® | 1-propanol, 2-[1-(3,3-dimethylcyclohexyl)ethoxy]-2-methyl-, 1-propanoate |
| NITRO | MOSKENE | 2,3-dihydro-1,1,3,3,5-pentamethyl-4,6-dinitro-1H-indene |
| NITRO | MUSK TIBETENE | 1-(1,1-dimethylethyl)-3,4,5-trimethyl-2,6-dinitrobenzene |
| NITRO | ORINOX | 1-[4-(1,1-dimethylethyl)-2,6-dimethylphenyl]-ethanone |
| NITRO | MUSK XYLENE | 1-(1,1-dimethylethyl)-3,5-dimethyl-2,4,6-trinitrobenzene |
| NITRO | MUSK KETONE | 1-[4-(1,1-dimethylethyl)-2,6-dimethyl-3,5-dinitrophenyl]-ethanone |
| NITRO | MUSK ALPHA | 1,3-dibromo-2-methoxy-4-methyl-5-nitrobenzene |

MACRO = macrocyclic musk fragrances
NITRO = nitro musk fragrances
POLY = polycyclic musk fragrances
ALICYC = alicyclic musk fragrance further individual fragrances or indeed a large number of further fragrances. Particularly advantageously, the compounds according to the invention can be combined with other fragrances, preferably selected from the fragrances already mentioned above, or mentioned below, in different quantity ratios to give novel fragrances or perfumes.

A further aspect of the present invention therefore relates to a method for intensifying an odor or several odors selected from the group consisting of fruity, floral, spicy, woody, musk and ambrette, comprising the following step:
(i) mixing one or more fragrance(s) with one, several or all of the notes selected from the group consisting of fruity, floral, spicy, woody, musk and ambrette with one or more compound(s) of the formula (I), preferably of the formula (IV), of a composition or fragrance mixture according to the invention, preferably a perfume oil, in a quantity which suffices to intensify the odor impression or odor impressions of the fragrance(s).

The compounds according to the invention, compositions according to the invention or fragrance mixtures according to the invention are preferably used for the production of perfumed products (perfumed articles). The sensory properties, like the material properties (such as solubility in common solvents and compatibility with common further components of such products) and the toxicological safety of the compound according to the invention emphasize its especial suitability for said use purposes.

Also a subject of the present invention therefore are perfumed products containing one or more compound(s) according to the invention, in particular one or more compound(s) of the formula (IV), a composition according to the invention or fragrance mixture, preferably in a sensorily effective quantity.

Preferred perfumed products according to the invention are selected from the group consisting of:

Perfume extracts, eaux de perfume, eaux de toilette, aftershave lotions, eaux de cologne, preshave products, splash colognes, perfumed wet wipes, perfumes for acidic, alkaline and neutral cleaning agents, detergents, laundry tablets, disinfectants, and of air fresheners, aerosol sprays, waxes and polishes, and toiletry products, bath oils, cosmetic emulsions, such as for example skin creams and lotions, sunshield creams and lotions, after-sun creams and lotions, hand creams and lotions, foot creams and lotions, depilatory creams and lotions, aftershave creams and lotions, tanning creams and lotions, hair care products such as for example hair sprays, hair gels, setting hair lotions, hair rinses, hair dyes, hair styling agents and hair straighteners, hair lotions, hair creams and lotions, deodorants and antiperspirants, decorative cosmetic products such as for example eye shadow, nail varnish, make-up, lipsticks, mascara, and of candles, lamp oils, incense sticks, insecticides, repellents and propellants.

Fragrance mixtures according to the invention containing the compounds according to the invention or a composition according to the invention as defined above can in general be used (e.g. in concentrated form, in solutions or in modified form described below) for the production of for example perfume extracts, eaux de perfume, eaux de toilette, aftershave lotions, eaux de cologne, pre-shave products, splash colognes and perfumed wet wipes and the perfuming of acidic, alkaline and neutral cleaning agents, such as for example floor cleaning agents, window cleaning agents, dishwashing agents, bath and sanitary cleaners, scouring agents, solid and liquid WC cleaners, powder and foam carpet cleaners, liquid detergents, powder detergents, laundry pretreatment agents such as bleaches, soaking agents and spot removers, fabric softeners, laundry soaps, laundry tablets, disinfectants, surface disinfectants and of air fresheners in liquid or gel form or applied onto a solid support, aerosol sprays, waxes and polishes such as furniture polishes, floor waxes, shoe creams and toiletry products such as for example solid and liquid soaps, shower gels, shampoos, shaving soaps, shaving foams, bath oils, cosmetic emulsions of the oil-in-water, water-in-oil and water-in-oil-in-water type such as for example skin creams and lotions, face creams and lotions, sun-screen creams and lotions, after-sun creams and lotions, hand creams and lotions, foot creams and lotions, depilatory creams and lotions, aftershave creams and lotions, tanning creams and lotions, hair care products such as for example hair sprays, hair gels, hair setting lotions, hair rinses, permanent and semi-permanent hair colorants, hair styling agents such as cold perms and hair straighteners, hair lotions, hair creams and lotions, deodorants and antiperspirants such as for example armpit sprays, roll-ons, deodorant sticks, deodorant creams, decorative cosmetic products such as for example eye shadow, nail varnishes, make-up, lipsticks and mascara, and of candles, lamp oils, incense sticks, insecticides, repellents and propellants.

The aforesaid fragrance mixtures according to the invention or the fragrance mixtures to be used according to the invention in the appropriate products can be used in liquid form, undiluted or diluted with a solvent for perfume products. Suitable solvents for this are for example ethanol, isopropanol, diethylene glycol monoethyl ether, glycerin, propylene glycol, 1,2-butylene glycol, dipropylene glycol, diethyl phthalate, triethyl citrate, isopropyl myristate etc. For said solvents, it applies that in the context of the present text in case of the presence of intrinsic olfactory properties, they are to be assigned exclusively to the component "solvent" and not to the "fragrances".

The compounds according to the invention contained in the perfumed products according to the invention, a composition according to the invention as described above or a fragrance mixture according to the invention as described above can here in a preferred embodiment be absorbed on a carrier substance which serves both for fine distribution of the fragrances in the product and also for controlled release during use. Such carriers can be porous inorganic materials such as light sulfate, silica gels, zeolites, gypsums, clays, clay granules, gas concrete etc. or organic materials such as woods and cellulose-based substances.

The compounds according to the invention contained in the perfumed products according to the invention, a composition according to the invention as described above or a fragrance mixture according to the invention as defined above can also be present micro-encapsulated, spray-dried, as inclusion complexes or as extrusion products, and be added in this form to the product or article to be perfumed.

Optionally the properties of the fragrance mixtures thus modified can be further optimized by so-called "coating" with suitable materials with regard to more selective perfume release, for which waxy plastics such as for example polyvinyl alcohol are preferably used.

The microencapsulation of the fragrance mixtures can for example be effected by the so-called coacervation method by means of capsule materials, e.g. of polyurethane-type materials or soft gelatins. The spray-dried perfume oils can be produced for example by spray-drying an emulsion or dispersion containing the perfume oil, wherein modified starches, proteins, dextrin and plant gums can be used as carrier substances. Inclusion complexes can be produced for example by introduction of dispersions of the fragrance mixture and cyclodextrins or urea derivatives into a suitable solvent, e.g. water. Extrusion products can result from melting the fragrance mixture with a suitable waxy substance and by extrusion with subsequent solidification, optionally in a suitable solvent, e.g. isopropanol.

The fragrance mixtures according to the invention can then, as already mentioned, be used in concentrated form, in solutions or in above-described modified form for the production of the corresponding perfumed articles according to the invention.

Additives with which the compounds according to the invention, a composition according to the invention as described above or a fragrance mixture according to the invention as described above, can preferably be combined are for example: preservatives, abrasive agents, anti-acne agents, anti-skin aging agents, antibacterial agents, anticellulitis agents, antidandruff agents, inflammation inhibitors, irritation-preventing agents, irritation-inhibiting agents, antimicrobial agents, antioxidants, astringents, perspiration-inhibiting agents, antiseptic agents, antistatic agents, binders, buffers, carrier materials, chelating agents, cell stimulants, cleansing agents, nurturing agents, depilatory agents, surface-active substances, deodorants, antiperspirants, plasticizers, emulsifiers, enzymes, essential oils, fibers, film-forming agents, fixatives, foaming agents, foam stabilizers, substances for preventing foaming, foam boosters, fungicides, gelling agents, gel-forming agents, hair care agents, hair styling agents, hair straighteners, hydrating agents, moisturizing substances, moisture-retaining substances, bleaching agents, strengthening agents, spot-removing agents, optical brighteners, impregnating agents, dirt-repellent agents, friction-reducing agents, lubricants, moisturizing creams, ointments, opacifiers, plasticizing agents, covering agents, polish, gloss agents, polymers, powders, proteins, lipid-replenishing agents, buffing agents, silicones, skin soothing agents, skin cleansing agents, skin nurturing agents, skin healing agents, skin whitening agents, skin protection agents, skin softening agents, cooling agents, skin cooling agents, warming agents, skin warming agents, stabilizers, UV absorbers, UV filters, detergents, fabric conditioners, suspending agents, skin tanning agents, thickeners, vitamins, oils, waxes, fats, phospholipids, saturated fatty acids, mono- or polyunsaturated fatty acids, α-hydroxy acids, polyhydroxy fatty acids, liquefiers, colorants, color protective agents, pigments, anticorrosion agents, aromas, flavor substances, polyols, surfactants, electrolytes, organic solvents or silicone derivatives.

Further aspects according to the invention in connection with compounds according to the invention, a composition according to the invention (as described above) or a fragrance mixture according to the invention (as described above) are explained below.

As already mentioned above, for surfactant-containing perfumed products the substantivity of a fragrance or a fragrance mixture as regards the retention thereof on the substrate, in particular hair or textile fibers, is a further important application technology requirement.

By addition of the compounds according to the invention or of a composition according to the invention (as described above) to a given fragrance mixture of only low substantivity and/or retention, these properties are particularly advantageously improved. Thus for example an aqueous laundry solution (or a corresponding detergent or shampoo or the like) which is indeed fruity, floral, and/or spicy-smelling, but owing to only inadequate substantivity of the perfume substances contained therein is unsuitable for imparting a fruity, floral and/or spicy odor to laundry (textile fibers) or hair, can by addition of the compounds according to the invention or of a composition according to the invention (as described above) be converted into a solution which outstandingly imparts a fruity, floral and/or spicy odor. The fruity, floral and/or spicy odor adheres for a long time to the treated substrates (hair or textile fibers).

The fragrance mixtures (as described above) containing compounds according to the invention or a composition according to the invention (as described above) are characterized by high substantivity. This effect is seen in particular on substrates such as skin, hair and textile fibers (e.g. wool, cotton, linen and synthetic fibers).

This effect is explained in more detail below in the context of the application technology examples.

Thus a perfumed product (as described above) which contains one or more surfactants is also a subject of the present invention.

For example, a perfumed product according to the invention is a weakly acidic, alkaline or neutral cleaning agent which is in particular selected from the group consisting of
general purpose cleaners, floor cleaners, window cleaners, washing up liquids, bath and sanitary cleaners, scouring cream, solid and liquid WC cleaners, powder and foam carpet cleaners, liquid detergents, powder detergents, laundry pretreatment agents such as bleaching agents, softeners and spot removers, laundry fabric softeners, laundry soaps, laundry tablets, disinfectants and surface disinfectants,
air fresheners in liquid or gel form, or applied on a solid carrier or as aerosol spray,
waxes or a polish which is in particular selected from the group consisting of furniture polishes, floor waxes and shoe creams,
and
toiletries, which is in particular selected from the group consisting of shower gels and shampoos.

The positive properties described contribute to the fact that the compounds according to the invention, a mixture according to the invention (as defined above) or a fragrance mixture according to the invention (as defined above) are especially preferably used in laundry and cleaning agents, hygiene or toiletry products, in particular in the field of body and hair care, cosmetics and the home.

Especially preferable perfumed products according to the invention are therefore laundry and cleaning agents, hygiene or toiletry products, in particular in the field of body and hair care, cosmetics and the home.

A fragrance mixture according to the invention is preferably produced according to the invention by mixing the compound according to the invention or a mixture according to the invention as defined above with the further fragrances and optionally further components of the fragrance mixture.

According to a preferred embodiment, a fragrance mixture according to the invention is produced as described above, wherein the compounds according to the invention are used in a quantity which suffices to procure, to modify and/or to intensify one or preferably both of the odor notes ambergris and wood in the fragrance mixture.

As already mentioned, the compounds according to the invention can be used as agents for endowing hair and/or textile fibers with one or both odor notes ambergris and/or wood.

Accordingly, a further aspect of the present invention relates to a method for endowing hair or textile fibers with one, several or all of the notes selected from the group consisting of fruity, floral, spicy, woody, musk and ambrette, comprising the following steps:

(i) preparing a fragrance mixture according to the invention, wherein the (further) fragrance(s) not corresponding to the formula (I) procure one, several or all of the notes fruity, floral, spicy, woody, musk and ambrette and the quantity of the compound(s) of the formula (I), preferably of the formula (IV), suffices to modify and/or to intensify one, several or all of the notes fruity, floral, spicy, woody, musk and ambrette, and (ii) applying the fragrance mixture onto the hair or the textile fibers.

For preferred components of a fragrance mixture to be used here, the aforesaid applies as appropriate.

The present invention will be explained in more detail below on the basis of selected examples.

EXAMPLES

Unless otherwise stated, contents and percentages relate to the respective weight.

Abbreviations Used:

Dipropylene glycol (DPG), diethyl phthalate (DEP), triethyl citrate (TEC).

For explanations of the product names of the fragrances, see e.g. S. Arctander, Perfume and Flavor Materials, Vol. I and II, Montclair, N. J., 1969, published by author, or H. Surburg, J. Panten, "Common Fragrance and Flavor Materials", 5$^{th}$. Ed., Wiley-VCH, Weinheim 2006.

Cis-cedranediol, which was obtained from (−)-α-cedrene by epoxidation and subsequent ring opening, was used. According to NMR investigation, the following structure for the diol is present:

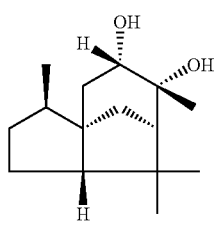 [SMILES: C[C@@H]1CC[C@H]2C(C)(C)[C@H]3C[C@@]12C[C@H](O)[C@]3(C)O]

Example 1

Reaction of cis-cedranediol with 1-methoxy-propan-2-one 24 g (0.1 mol) of cis-cedranediol (26 g with a GC content of 92% were used), 127.6 g (1.45 mol) of 1-methoxy-propan-2-one, 31.8 g (0.3 mol) of trimethyl orthoformate and 0.4 g of concentrated sulfuric acid were stirred for 24 hours at 10° C. After the end of the reaction, methyl tert.-butyl ether was added, washed with a 5% sodium hydrogen carbonate solution and the low-boilers distilled off. After addition of n-hexane, unreacted cis-cedranediol crystallized out, and was removed by filtration. After concentration of the filtrate, 30.4 g of crude product were obtained. According to GC analysis, the content of the compounds of the formulae (VIII) and (IX) in the product obtained was in total 51% (corresponding to 50% of the theoretical yield). By dissolving the crude product in dipropylene glycol (DPG), a solution with a content of 10 wt. % of compounds of the formulae (VIII) and (IX) (with a ratio of (VIII):(IX)=1:2.3) was produced from this.

For analytical tests, from the crude product the stereoisomeric compounds of the formulae (VIII) and (IX) were separated from one another by liquid chromatography on silica gel 60 (0.04-0.063 mm) with the eluent cyclohexane/ethyl acetate (60/1). The compound of the formula (VIII) was obtained with a purity of 99.4% and the compound of the formula (IX) with a purity of 96.9%.

Compound of the formula (VIII):

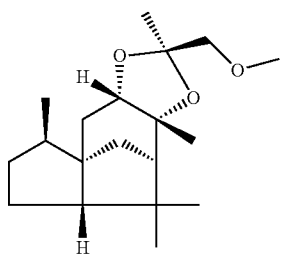 [SMILES: COC[C@]1(C)O[C@H]2C[C@@]34C[C@H](C(C)(C)[C@@H]3CC[C@H]4C)[C@@]2(C)O1]

$^1$H-NMR (400 MHz, C$_6$D$_6$): □ 3.95 (dd, J=8.5, 7.2 Hz, 1H), 3.58 (dq, J=10.3, 0.5 Hz, 1H), 3.51 (dq, J=10.3, 0.5 Hz, 1H), 3.28 (s, 3H), 2.23 (dt, J=12.1, 1.0 Hz, 1H), 1.98 (d, J=4.5 Hz, 1H), 1.86-1.76 (m, 2H), 1.754 (q, J=0.3 Hz, 3H), 1.75-1.69 (m, 1H), 1.62 (h, J=6.9 Hz, 1H), 1.49 (s, 3H), 1.44 (ddd, J=12.3, 4.8, 2.0 Hz, 1H), 1.42-1.35 (m, 1H), 1.36-1.25 (m, 2H), 1.23-1.11 (m, 1H), 0.96 (s, 3H), 0.89 (s, 3H), 0.76 (d, J=7.1 Hz, 3H) ppm.

$^{13}$C-NMR (C$_6$D$_6$): □ 109.86, 85.13, 80.02, 78.58, 59.15, 58.70, 57.83, 52.53, 42.36, 42.23, 41.65, 38.91, 36.17, 31.17, 28.79, 28.19, 25.61, 25.19, 15.59 ppm.

Odor: very strong ambergris, wood, reminiscent of white ambergris, very long adhesion Compound of the Formula (IX):

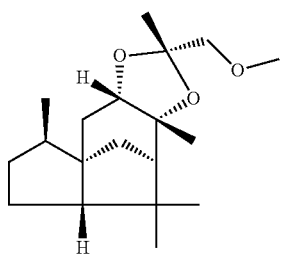 [SMILES: COC[C@@]1(C)O[C@H]2C[C@@]34C[C@H](C(C)(C)[C@@H]3CC[C@H]4C)[C@@]2(C)O1]

$^1$H-NMR (400 MHz, C$_6$D$_6$): □ 3.99 (dd, J=8.9, 6.8 Hz, 1H), 3.60 (d, J=10.2 Hz, 1H), 3.57 (d, J=10.2 Hz, 1H), 3.26 (d, J=0.5, 3H), 2.23 (d, J=11.9 Hz, 1H), 1.99 (d, J=4.5 Hz, 1H), 1.81 (ddd, J=13.5, 8.9, 2.5 Hz, 1H), 1.74 (s, 3H), 1.78-1.68 (m, 2H), 1.64 (h, J=6.8 Hz, 1H), 1.52 (s, 3H), 1.42 (ddd, J=12.0, 4.6, 2.6 Hz, 1H), 1.41-1.35 (m, 1H), 1.35-1.24 (m, 2H), 1.23-1.11 (m, 1H), 0.96 (s, 3H), 0.88 (s, 3H), 0.78 (d, J=7.1 Hz, 3H) ppm.

$^{13}$C-NMR (C$_6$D$_6$): □ 109.85, 84.90, 79.33, 78.73, 59.15, 58.73, 57.86, 52.52, 42.38, 42.32, 41.99, 38.74, 36.24, 31.14, 28.76, 28.11, 25.93, 25.63, 15.63 ppm.

Odor: weak ambergris

Example 2

Reaction of Cis-Cedranediol with Methoxyacetaldehyde Dimethyl Acetal 24 g (0.1 mol) of cis-cedranediol (26 g with a GC content of 92% were used), 127.6 g (1.45 mol) of methoxyacetaldehyde dimethyl acetal and 0.4 g of concentrated sulfuric acid were stirred for 24 hours at 10° C. After the end of the reaction, methyl tert.-butyl ether was added, washed with a 5% sodium hydrogen carbonate solution and the low-boilers distilled off. After addition of n-hexane, unreacted cis-cedranediol crystallized out, and was removed by filtration. After concentration of the filtrate, 30.4 g of crude product were obtained. According to GC analysis, the content of the compounds of the formulae (X) and (XI) in the product obtained was in total 51% (corresponding to 50% of the theoretical yield). By dissolving the crude product in dipropylene glycol (DPG), a solution with a content of 10 wt. % of compounds of the formulae (X) and (XI) (with a ratio of (X):(XI)=1:6.2) was produced from this.

For analytical tests, from the crude product the stereoisomeric compounds of the formulae (X) and (XI) were separated from one another by liquid chromatography on silica gel 60 (0.04-0.063 mm) with the eluent cyclohexane/ethyl acetate (60/1). The compound of the formula (X) was obtained with a purity of 99.4% and the compound of the formula (XI) with a purity of 96.9%.

Compound of the Formula (X):

MS: m/z: 41 (24), 43 (20), 45 (16), 55 (21), 69 (64), 93 (17), 95 (17), 105 (50), 119 (100), 133 (58), 147 (26), 203 (86), 249 (25)

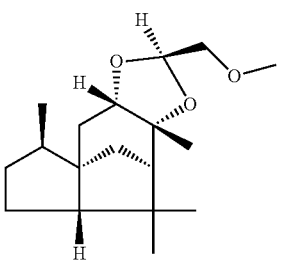 [SMILES: COC[C@@H]1O[C@H]2C[C@@]34C[C@H](C(C)(C)[C@@H]3CC[C@H]4C)[C@@]2(C)O1]

Odor: strong ambergris, wood

Compound of the formula (XI):

MS: m/z: 41 (23), 43 (19), 45 (16), 55 (23), 69 (60), 93 (17), 95 (17), 105 (49), 119 (100), 133 (57), 147 (24), 203 (83), 249 (26)

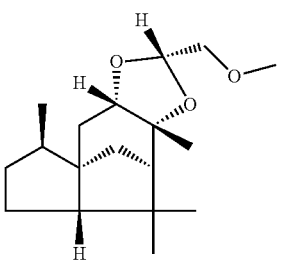 [SMILES: COC[C@H]1O[C@H]2C[C@@]34C[C@H](C(C)(C)[C@@H]3CC[C@H]4C)[C@@]2(C)O1]

Odor: weak ambergris

In the following perfume formulae and application examples, in each case solutions with the stated content were used, wherein the weight ratio of the compound of the formula (VIII) to the compound of the formula (IX) was 3:8 and the weight ratio of (X) to (XI) was 3:8.

Perfume Oil Example according to the invention P1:

|  | Ref-1 | P1 |
|---|---|---|
| HEXENAL DIMETHYL ACETAL, 2,2,5-TRIMETHYL-4- | 10 | 10 |
| HEXADECEN-1,16-OLIDE, 7(9)Z- | 15 | 15 |
| CYCLOHEXADECENONE, (8E/Z)- + CYCLOHEXADECENONE, (7E)- | 140 | 140 |
| BUT-2-EN-1-ONE, 1-(2,6,6-TRIMETHYL-CYCLOHEX-3-ENYL)- (E) 10% DPG | 10 | 10 |
| ETHANEDIOL BRASSYLATE | 120 | 120 |
| NONADIEN-3-OL, 3,7-DIMETHYL-1,6- | 30 | 30 |
| PYRANOL, 2-ISOBUTYL-4-METHYL-4-TETRAHYDRO- (E/Z) | 40 | 40 |
| 5-HEXENYL BUTYRATE, 2-METHYL- | 5 | 5 |
| GERANYL ACETATE | 40 | 40 |
| METHYL DIHYDROJASMONATE | 400 | 400 |
| 2-(1-(3,3-DIMETHYLCYCLOHEXYL)-ETHOXY-2-METHYLPROPYL PROPIONATE | 30 | 30 |
| 3Z-HEXENYL ACETATE | 5 | 5 |
| 3Z-HEXENYL SALICYLATE | 20 | 20 |
| BICYCLO[4.4.0]DECENE, 3,4,10,10-TETRAMETHYL-3-HYDROXYETHYL-1(6) | 50 | 50 |
| CYCLOHEXANONE, 3,3,5,5-TETRAMETHYL-4-(1-ETHOXYVINYL)- | 10 | 10 |
| 3Z-HEXENYL METHYL CARBONATE, 10% in DPG | 10 | 10 |
| MANDARIN OIL | 20 | 20 |
| 2(3H)-FURANONE, 5-HEXYL-DIHYDRO-4-METHYL- (E/Z) | 5 | 5 |
| PRENYL ACETATE | 5 | 5 |
| TRICYCLO(5.2.1.0)DECANE, 8-FORMYL- | 15 | 15 |
| DIOXOLE, 4H-4A,9-METHANOAZULENO(5,6-D)-OCTAHYDRO-2,2,5,8,9A-HEXAMETHYL-, 1,3-(Ambrocenide ®), 0.1% in DPG | 20 | 0 |
| (Compound of the formula (VIII)), 0.1% in DPG | 0 | 20 |
| TOTAL | 1000 | 1000 |

The comparative example (Ref-1) with Ambrocenide® smells fresh, fruity and transparent. In perfume oil P1, the compound of the formula (VIII) imparts to the composition an elegance and more pronounced fruitiness.

Perfume Oil Example According to the Invention P2:

|  | Ref-2 | P2 |
|---|---|---|
| UNDECALACTONE, GAMMA- | 2 | 2 |
| HEXADECEN-1,16-OLIDE, 7(9)Z- | 10 | 10 |
| CYCLOHEXADECENONE, (8E/Z)- + CYCLOHEXADECENONE, (7E)- | 100 | 100 |
| CARDAMOM OIL CEYLON | 2 | 2 |
| INDAN-4-ONE, 1,1,2,3,3-PENTAMETHYL-TETRAHYDRO- | 15 | 15 |
| CEDARWOOD OIL VIRGINIA | 100 | 100 |
| DAMASCONE, -BETA-, 10% in DPG | 2 | 2 |
| METHYL DIHYDROJASMONATE | 210 | 210 |
| BICYCLO[4.4.0]DECENE, 3,4,10,10-TETRAMETHYL-3-HYDROXYETHYL-1(6) | 300 | 300 |
| IRALDEIN, GAMMA- | 60 | 60 |
| CYCLOHEXANONE, 3,3,5,5-TETRAMETHYL-4-(1-ETHOXYVINYL)- | 10 | 10 |
| CYCLOPENTADECENONE, 3-METHYL-5E- | 20 | 20 |
| PATCHOULI OIL | 5 | 5 |
| PENTEN-2-OL, 3,3-DIMETHYL-5-(2,2,3-TRIMETHYL-3-CYCLOPENTENYL)-4- | 20 | 20 |
| PENTANOL, 3-METHYL-5-(2,2,3-TRIMETHYL-3-CYCLOPENTENYL)-2- + HEXANOL, 6-(2,2,3-TRIME-3-CYCLOPENTENYL)-3- | 80 | 80 |
| VANILLIN | 2 | 2 |
| ISOLONGIFOLANONE ETHANEDIOL KETAL | 30 | 30 |
| CINNAMON BARK OIL CEYLON | 2 | 2 |
| DIOXOLE, 4H-4A,9-METHANOAZULENO(5,6-D)-OCTAHYDRO-2,2,5,8,8,9A-HEXAMETHYL-, 1,3-(Ambrocenide ®), 0.1% in DPG | 30 | 0 |
| (Compound of the formula (VIII)), 0.1% in DPG | 0 | 30 |
| TOTAL | 1000 | 1000 |

The comparative example (Ref-2) with Ambrocenide® smells floral-spicy with dry woody accents. In perfume oil P2, the spicy note is supported by the compound of the formula (VIII), so that the whole composition appears more peppery and more characterful.

Perfume Oil Example According to the Invention P3:

|  | Ref-3 | P3 |
|---|---|---|
| HEXENAL DIMETHYL ACETAL, 2,2,5-TRIMETHYL-4- | 10 | 10 |
| BENZODIOXEPINONE, 7-METHYL-3,4-DIHYDRO-3- | 10 | 10 |
| PROPANAL, 2-METHYL-3-(4-METHOXYPHENYL)- | 5 | 5 |
| CITRONELLOL, BETA- | 20 | 20 |
| LEMON OIL | 15 | 15 |
| ALLYL CYCLOHEXYLOXYACETATE, 10% in DPG | 10 | 10 |
| DAMASCONE, TRANS-ALPHA-, 1% IN DPG | 20 | 20 |
| BUT-2-EN-1-ONE, 1-(2,6,6-TRIMETHYL-CYCLOHEX-3-ENYL)-(E), 10% in DPG | 5 | 5 |
| DECALACTONE GAMMA, 10% in DPG | 15 | 15 |
| ETHANEDIOL BRASSYLATE | 80 | 80 |
| NONADIEN-3-OL, 3,7-DIMETHYL-1,6- | 70 | 70 |
| PHENOL, 2-METHOXY-4-(2-PROPENYL)- | 5 | 5 |
| PYRANOL, 2-ISOBUTYL-4-METHYL-4-TETRAHYDRO- (E/Z) | 80 | 80 |
| 5-HEXENYL BUTYRATE, 2-METHYL- | 15 | 15 |
| METHYL DIHYDROJASMONATE | 250 | 250 |
| PROPANAL, 2-PIPERONYL- | 30 | 30 |
| 3Z-HEXENYL SALICYLATE | 5 | 5 |
| INDOLE, 10% in DPG | 10 | 10 |
| IRALDEIN, GAMMA- | 30 | 30 |
| BICYCLO[4.4.0]DECENE, 3,4,10,10-TETRAMETHYL-3-HYDROXYETHYL-1(6) | 80 | 80 |
| PENTADECANOLIDE, 1,15- | 20 | 20 |
| HEPTENAL, 2,6-DIMETHYL-5-, 10% in DPG | 3 | 3 |
| PYRIDINE, 4-DECYL-, 1% in DPG | 2 | 2 |
| CYCLOHEXENE, 2,4-DIMETHYL-1-FORMYL-3-, 10% in DPG | 10 | 10 |
| DIOXOLE, 4H-4A,9-METHANOAZULENO(5,6-D)-OCTAHYDRO-2,2,5,8,8,9A-HEXAMETHYL-, 1,3- (Ambrocenide ®), 0.1% in DPG | 5 | 0 |
| (Compound of the formula (X)), 0.1% in DPG | 0 | 5 |
| TOTAL | 805 | 805 |

The comparative example (Ref-3) with Ambrocenide® impresses through its transparent freshness. In perfume oil P3, through the compound of the formula (X) it is achieved that the composition is perceived as more cosmetically nurturing with more volume.

Perfume Oil Example According to the Invention P4:

|  | Ref-4 | P4 |
|---|---|---|
| NAPHTHO[2.1-B]FURAN, DODECAHYDRO-3A.6.6.9A-TETRAMETHYL- | 5 | 5 |
| BENZOIN SIAM ABS., 50% IN DPG | 10 | 10 |
| BENZYL SALICYLATE | 20 | 20 |
| BERGAMOT OIL | 50 | 50 |
| CEDRYL METHYL ETHER | 40 | 40 |
| CISTUS LABDANUM | 35 | 35 |
| CISTUS OIL SPAN., 10% in DPG | 10 | 10 |
| DAMASCONE, TRANS-ALPHA-, 1% in DPG | 20 | 20 |
| MYRCENOL, DIHYDRO- | 30 | 30 |
| ETHANEDIOL BRASSYLATE | 120 | 120 |
| METHYL BENZOATE, 2,4-DIHYDROXY-3,6-DIMETHYL-, 1% in DPG | 20 | 20 |
| PYRANOL, 2-ISOBUTYL-4-METHYL-4-TETRAHDRO- (E/Z) | 20 | 20 |
| PENTADECEN-1,15-OLIDE, (11E/Z)- + PENTADECEN-1,15-OLIDE, 12E- | 30 | 30 |
| METHYL DIHYDROJASMONATE | 300 | 300 |
| BICYCLO[4.4.0]DECENE, 3,4,10,10-TETRAMETHYL-3-HYDROXYETHYL-1(6) | 75 | 75 |
| ISOBUTYLQUINOLINE, 10% in DPG | 3 | 3 |
| CYCLOHEXANONE, 3,3,5,5-TETRAMETHYL-4-(1-ETHOXYVINYL)- | 30 | 30 |
| LABDANUM ABSOLUTE | 20 | 20 |
| LINALYL ACETATE | 50 | 50 |
| MANDARIN OIL | 10 | 10 |
| CYCLOPENTADECENONE, 3-METHYL-5E- | 10 | 10 |
| CLARY SAGE OIL | 10 | 10 |
| OLIBANUM COEUR, 50% in TEC | 5 | 5 |

|  | Ref-4 | P4 |
|---|---|---|
| PATCHOULI OIL | 20 | 20 |
| PYRIDINE, 4-DECYL-, 1% in DPG | 2 | 2 |
| BUTENOL, 2-ETHYL-4-(2,2,3-TRI-METHYL-3-CYCLOPENTENYL)-2E- | 5 | 5 |
| VANILLIN | 30 | 30 |
| DIOXOLE, 4H-4A,9-METHANOAZULENO(5,6-D)-OCTAHYDRO-2,2,5,8,8,9A-HEXAMETHYL-, 1,3-(Ambrocenide ®), 0.1% in DPG | 20 | 0 |
| (Compound of the formula (X)), 0.1% in DPG | 0 | 20 |
| TOTAL | 1000 | 1000 |

The comparative example (Ref-4) with Ambrocenide® impresses through a beautiful wood note. In perfume oil P4, the compound of the formula (X) imparts more volume to the composition and the tobacco note is intensified.

Perfume Oil Example According to the Invention P5:

|  | Ref-5 | P5 |
|---|---|---|
| CYCLOHEXADECENONE, (8E/Z)- + CYCLOHEXADECENONE, (7E)- | 200 | 200 |
| MUGWORT OIL | 10 | 10 |
| BERGAMOT OIL | 60 | 60 |
| CEDRYL METHYL ETHER | 40 | 40 |
| CISTUS OIL SPAN., 10% in DPG | 10 | 10 |
| LEMON OIL | 20 | 20 |
| COUMARIN | 40 | 40 |
| ALLYL CYCLOHEXYLOXYACETATE, 10% in DPG | 5 | 5 |
| MYRCENOL, DIHYDRO- | 50 | 50 |
| ETHANEDIOL BRASSYLATE | 120 | 120 |
| METHYL BENZOATE, 2,4-DIHYDROXY-3,6-DIMETHYL-, 10% in DPG | 20 | 20 |
| METHYL DIHYDROJASMONATE | 30 | 30 |
| IRALDEIN, GAMMA- | 20 | 20 |
| BICYCLO[4.4.0]DECENE, 3,4,10,10-TETRAMETHYL-3-HYDROXYETHYL-1(6) | 120 | 120 |
| SPEARMINT OIL, 10% in DPG | 10 | 10 |
| LAVENDER OIL | 10 | 10 |
| LINALOOL | 20 | 20 |
| LINALYL ACETATE | 20 | 20 |
| INDENO[1.2-D]-M-DIOXIN, 2,4-DIMETHYL-TETRAHYDRO- | 90 | 90 |
| CLARY SAGE ABSOLUTE | 5 | 5 |
| CLOVE FLOWER OIL | 10 | 10 |
| VANILLIN | 20 | 20 |
| DIOXOLE, 4H-4A,9-METHANOAZULENO(5,6-D)-OCTAHYDRO-2,2,5,8,8,9A-HEXAMETHYL-, 1,3-(Ambrocenide ®), 0.1% in DPG | 20 | 0 |
| (Compound of the formula (VIII)), 0.1% in DPG | 0 | 20 |
| TOTAL | 950 | 950 |

The comparative example (Ref-5) with Ambrocenide® has a very radiant and intense lavender effect. In perfume oil P5, through the compound of the formula (VIII), the whole composition becomes more naturally lavender-like and as a result appears higher quality with more volume.

Perfume Oil Example According to the Invention P6:

|  | Ref-6 | P6 |
|---|---|---|
| HEXADECEN-1,16-OLIDE, 7(9)Z- | 20 | 20 |
| CYCLOHEXADECENONE, (8E/Z)- + CYCLOHEXADECENONE, (7E)- | 200 | 200 |
| INDAN-4-ONE, 1,1,2,3,3-PENTAMETHYL-TETRAHYDRO- | 20 | 20 |
| ETHANEDIOL BRASSYLATE | 150 | 150 |
| 5-HEXENYL BUTYRATE, 2-METHYL- | 5 | 5 |
| PENTADECEN-1,15-OLIDE, (11E/Z)- + PENTADECEN-1,15-OLIDE, 12E- | 90 | 90 |
| METHYL DIHYDROJASMONATE | 210 | 210 |
| BICYCLO[4.4.0]DECENE, 3,4,10,10-TETRAMETHYL-3-HYDROXYETHYL-1(6) | 200 | 200 |
| CYCLOHEXANONE, 3,3,5,5-TETRAMETHYL-4-(1-ETHOXYVINYL)- | 20 | 20 |
| PENTEN-2-OL, 3,3-DIMETHYL-5-(2,2,3-TRIMETHYL-3-CYCLOPENTENYL)-4- | 5 | 5 |
| ISOLONGIFOLANONE ETHANEDIOL KETAL | 70 | 70 |
| DIOXOLE, 4H-4A,9-METHANOAZULENO(5,6-D)-OCTAHYDRO-2,2,5,8,8,9A-HEXAMETHYL-, 1,3-(Ambrocenide ®), 0.1% in DPG | 10 | 0 |
| (Compound of the formula (VIII)), 0.1% in DPG | 0 | 10 |
| TOTAL | 1000 | 1000 |

The comparative example (Ref-6) with Ambrocenide® possesses a cool transparency paired with a dry woodiness. In perfume oil P6, the compound of the formula (VIII) imparts to the whole composition a more pronounced harmony and warmth, wherein the fruitiness is intensified (pushed) as far as a beautiful plum note paired with tobacco effects.

Perfume Oil Example According to the Invention P7:

|  | Ref-7 | P7 |
|---|---|---|
| NAPHTHO[2.1-B]FURAN, DODECAHYDRO-3A.6.6.9A-TETRAMETHYL- | 5 | 5 |
| BENZYL SALICYLATE | 50 | 50 |
| BERGAMOT OIL | 50 | 50 |
| COUMARIN | 5 | 5 |

| | Ref-7 | P7 |
|---|---|---|
| DAMASCONE, TRANS-ALPHA-, 1% in DPG | 20 | 20 |
| DECALACTONE GAMMA, 10% in DPG | 15 | 15 |
| ETHANEDIOL BRASSYLATE | 30 | 30 |
| NONADIEN-3-OL, 3,7-DIMETHYL-1,6- | 60 | 60 |
| 3,7-DIME-1,6-NONADIEN-3-YL ACETATE | 50 | 50 |
| PYRANOL, 2-ISOBUTYL-4-METHYL-4-TETRAHYDRO- (E/Z) | 70 | 70 |
| 5-HEXENYL BUTYRATE, 2-METHYL- | 5 | 5 |
| BICYCLO[2.2.2]OCTENE, 6-ME-8-ISOPROPYL-2(3)-(1,3-DIOXOLAN-2-YL | 5 | 5 |
| METHYL DIHYDROJASMONATE | 280 | 280 |
| PROPANAL, 2-PIPERONYL- | 20 | 20 |
| BENZALDEHYDE, 3,4-METHYLENEDIOXY- | 10 | 10 |
| 2-(1-(3,3-DIMETHYLCYCLOHEXYL)-ETHOXY-2-METHYLPROPYL PROPIONATE | 60 | 60 |
| 3Z-HEXENYL SALICYLATE | 5 | 5 |
| BICYCLO[4.4.0]DECENE, 3,4,10,10-TETRAME-3-HYDROXYETHYL-1(6) | 120 | 120 |
| PENTADECANOLIDE, 1,15- | 30 | 30 |
| MANDARIN OIL | 20 | 20 |
| CYCLOPENTADECENONE, 3-METHYL-5E- | 3 | 3 |
| BUTANOL, 2-METHYL-4-PHENYL-2- | 10 | 10 |
| PYRIDINE, 4-DECYL-, 1% in DPG | 2 | 2 |
| PENTEN-2-OL, 3,3-DIMETHYL-5-(2,2,3-TRIMETHYL-3-CYCLOPENTENYL)-4- | 20 | 20 |
| CYCLOHEXANOL, 4-(3-METHYL-BUTYL)- (E/Z) | 15 | 15 |
| VANILLIN | 20 | 20 |
| DIOXOLE, 4H-4A,9-METHANOAZULENO(5,6-D)-OCTAHYDRO-2,2,5,8,8,9A-HEXAMETHYL-, 1,3-(Ambrocenide ®), 0.1% in DPG | 5 | 0 |
| (Compound of the formula (VIII)), 0.1% in DPG | 0 | 5 |
| DIPROPYLENE GLYCOL | 15 | 15 |
| TOTAL | 1000 | 1000 |

Through the replacement of Ambrocenide® of the comparative example (Ref-7) by the compound of the formula (VIII), the whole composition P7 has a more voluminous, more elegant and thus also higher quality effect, perfume oil P7 has a more complex effect and the coumarin note is very beautifully harmonized.

Perfume Oil Example According to the Invention P8:

| | Ref-8 | P8 |
|---|---|---|
| Ethyl acetoacetate | 60 | 60 |
| Propanal, 2-methyl-2-(4-ethylbenzyl)- | 25 | 25 |
| Cyclohexene, 2,4-dimethyl-1-formyl-3- (E/Z) | 15 | 15 |
| Hexenol Cis-3 | 130 | 130 |
| 3Z-hexenyl methyl carbonate | 20 | 20 |
| Allyl cyclohexyloxyacetate | 25 | 25 |
| Benzenemethanol, .alpha.-methyl-, 1-acetate | 40 | 40 |
| Linalyl acetate | 80 | 80 |
| Myrcenol, Dihydro- | 650 | 650 |
| Mandarin oil | 260 | 260 |
| Grapefruit oil | 260 | 260 |
| Hexenal dimethyl acetal, 2,2,5-trimethyl-4- | 170 | 170 |
| Methyl anthranilate, 10% DPG | 155 | 155 |
| Cardamom oil | 5 | 5 |
| Red Berry Extract | 25 | 25 |
| Nutmeg oil | 20 | 20 |
| Ethyl butyrate, 10% DPG | 10 | 10 |
| Undecalactone, gamma- | 65 | 65 |
| Ethyl pentanoate, 2-methyl-, 10% DPG | 15 | 15 |
| 2-propen-1-yl heptanoate | 40 | 40 |
| Ethylmaltol | 15 | 15 |
| Benzenepropanal, alpha-methyl-4-(1,1-dimethylethyl)- | 250 | 250 |
| 1,3-Benzodioxol-5-propanal, alpha-methyl- | 200 | 200 |
| Hydroxycitronellal | 200 | 200 |
| 4-methyl-2-(2-methylpropyl)oxan-4-ol | 260 | 260 |
| 1,6-octadien-3-ol, 3,7-dimethyl- | 40 | 40 |
| Nonadien-3-ol, 3,7-dimethyl-1,6- | 130 | 130 |
| 1,1-dimethyl-2-phenylethyl butyrate | 65 | 65 |
| Phenylethyl alcohol | 40 | 40 |
| 2-phenoxyethyl propionate, 2-methyl- | 40 | 40 |
| 2-buten-1-one, 1-(2.6.6-trimethyl-2-cyclohexen-1-yl)- (E) | 40 | 40 |
| 2-buten-1-one, 1-(2.6.6-trimethyl-1.3-cyclohexadien-1-yl)- | 5 | 5 |
| Methyl dihydrojasmonate | 390 | 390 |
| 3-buten-2-one, 3-methyl-4-(2.6.6-trimethyl-2-cyclohexen-1-yl)- | 220 | 220 |
| Vanillin | 230 | 230 |
| Cinnamon bark oil | 15 | 15 |
| 2H-1-benzopyran-2-one | 200 | 200 |
| Cyclohexanol acetate, 4-(1,1-dimethylethyl)- (Z) | 50 | 50 |
| Cedarwood oil | 15 | 15 |
| Bicyclo[4.4.0]decene, 3,4,10,10-tetramethyl-3-hydroxyethyl-1(6) | 1,500 | 1,500 |
| Cyclododecane, (ethoxymethoxy)- | 300 | 300 |
| 2-buten-1-ol, 2-ethyl-4-(2.2.3-trimethyl-3-cyclo-penten-1-yl)- (2E) | 130 | 130 |
| Dioxole, 4H-4a,9-methanoazuleno(5,6-d)-octa-hydro-2,2,5,8,8,9a-hexamethyl-, 1,3-(Ambrocenide ®), 10.0% in DPG | 30 | 0 |
| (Compound of the formula (X)), 10.0% in DPG | 0 | 30 |
| 5H-3.5a-Epoxynaphth[2.1-c]oxepine, dodecahydro-3.8.8.11a-tetramethyl- | 1,200 | 1,200 |
| Naphtho[2.1-b]furan, dodecahydro-3a.6.6.9a-tetramethyl- | 220 | 220 |
| Dipropylene glycol | 175 | 175 |
| TOTAL | 8,030 | 8,030 |

The comparative example Ref-8 with Ambrocenide® is characterized by the contradiction between fresh woody notes and sweet balsamic aspects. The replacement of Ambrocenide® by the compound of the formula (X) imparts to the whole composition more impact, volume and character paired with velvety-powdery aspects.

Perfume Oil Example According to the Invention P9:

|  | Ref-9 | P9 |
| --- | --- | --- |
| Undecenal, 2,6,10-trimethyl-9- | 15.00 | 15.00 |
| Propanal, 2-methyl-2-(4-ethylbenzyl)- | 3.00 | 3.00 |
| Cis-3 hexenyl acetate | 3.00 | 3.00 |
| Cyclohexene, 2,4-dimethyl-1-formyl-3- (E/Z) | 2.00 | 2.00 |
| Tricyclo(5.2.1.0)decane, 8-formyl- | 2.00 | 2.00 |
| Allyl cyclohexyloxyacetate | 4.00 | 4.00 |
| Heptenal, 2,6-dimethyl-5- | 2.00 | 2.00 |
| Identoil ® Bergamot | 45.00 | 45.00 |
| Myrcenol, Dihydro- | 90.00 | 90.00 |
| 2.6-octadienal, 3.7-dimethyl- (2E/Z) | 10.00 | 10.00 |
| 2-pentenonitrile, 3-methyl-5-phenyl- (2E/Z) | 3.00 | 3.00 |
| Orange oil | 30.00 | 30.00 |
| Hexenal dimethyl acetal, 2,2,5-trimethyl-4- | 2.00 | 2.00 |
| Lavandin oil | 10.00 | 10.00 |
| Cardamom oil | 1.00 | 1.00 |
| Ethyl pentanoate, 2-methyl-, 10% DPG | 10.00 | 10.00 |
| Benzenepropanal, alpha-methyl-4-(1.1-dimethylethyl)- | 40.00 | 40.00 |
| 2H-1.5-benzodioxepin-3(4H)-one, 7-methyl- | 20.00 | 20.00 |
| Benzenepropanol, beta.beta.3-trimethyl- | 40.00 | 40.00 |
| Geranium oil | 2.00 | 2.00 |
| 3-buten-2-one, 1-(2.4.4-trimethyl-2-cyclohexen-1-yl)- (2E) | 10.00 | 10.00 |
| alpha-hexylcinnamaldehyde | 60.00 | 60.00 |
| Methyl cyclopentaneacetate, 3-oxo-2-pentyl- (E) | 90.00 | 90.00 |
| Propanonitrile, 3-(3-hexenyloxy)- (Z) | 2.00 | 2.00 |
| 3-buten-2-one, 4-(2.6.6-trimethyl-1-cyclohexen-1-yl)- | 5.00 | 5.00 |
| Benzene, 1-methoxy-4-(1-propenyl)- (E) | 10.00 | 10.00 |
| Ethanone, 1-(2-benzofuranyl)- | 2.00 | 2.00 |
| Cyclohexanol acetate, 4-(1.1-dimethylethyl)- (Z) | 30.00 | 30.00 |
| Cedarwood Oil (cedarwood oil) | 15.00 | 15.00 |
| Cyclohexanepropanol, alpha-ethyl-2.2.6-trimethyl- (E/Z) | 30.00 | 30.00 |
| Bicyclo[4.4.0]decene, 3,4,10,10-tetramethyl-3-hydroxyethyl-1(6) | 100.00 | 100.00 |
| Cyclododecane, (ethoxymethoxy)- | 30.00 | 30.00 |
| Patchouli oil | 10.00 | 10.00 |
| 2-buten-1-ol, 2-ethyl-4-(2.2.3-trimethyl-3-cyclopenten-1-yl)- (2E) | 30.00 | 30.00 |
| Methyl benzoate, 2,4-dihydroxy-3,6-dimethyl- | 3.00 | 3.00 |
| Tetramethyl dodecahydro-3a,6,6,9a-naphtho(2,1-b)furan | 12.00 | 12.00 |
| Isolongifolanone ethanediol ketal | 50.00 | 50.00 |
| Dioxole, 4H-4a,9-methanoazuleno(5,6-d)-octahydro-2,2,5,8,8,9a-hexamethyl-, 1,3-(Ambrocenide ®), 10.0% in DPG | 2.00 | 0 |
| (Compound of the formula (X)), 10.0% in DPG | 0 | 2.00 |
| Pentadecanolide, 1,15- | 30.00 | 30.00 |
| Cyclohexadecenone, 8E/Z- | 120.00 | 120.00 |
| Dipropylene glycol | 25.00 | 25.00 |
| TOTAL | 1,000.00 | 1,000.00 |

The comparative example Ref-9 with Ambrocenide® is a modern fougere type with a watery citrus top note and a woody base. Through the replacement of Ambrocenide® by the compound of the formula (X), the white wood, as well as cedar- and sandalwood aspect, is intensified.

Perfume Oil Example According to the Invention P10:

|  | Ref-10 | P10 |
| --- | --- | --- |
| Undecenal, 2,6,10-trimethyl-9- | 8 | 8 |
| 10-Undecenal | 8 | 8 |
| Cyclohexene, 2,4-dimethyl-1-formyl-3- (E/Z) | 5 | 5 |
| 3Z-hexenyl methyl carbonate | 8 | 8 |
| Indeno[1.2-d]-1.3-dioxin, 4.4a.5.9b-tetrahydro-2.4-dimethyl- | 70 | 70 |
| Cyclohexanol acetate, 3.3.5-trimethyl- | 20 | 20 |
| Orange oil | 20 | 20 |
| Methyl naphthyl ketone beta | 5 | 5 |
| Ethanone, 1-(3-methyl-2-benzofuranyl)- | 2 | 2 |
| 2-butanone, 4-(4-hydroxyphenyl)- | 1 | 1 |
| Peach Base | 8 | 8 |
| Pyranol, 2-isobutyl-4-methyl-4-tetrahydro- (E/Z) | 10 | 10 |
| 1.6-octadien-3-ol, 3.7-dimethyl- | 90 | 90 |
| 2H-pyran, tetrahydro-2-methyl-2-(2-methyl-1-propenyl)- (E/Z) | 3 | 3 |
| 2-phenylethanol | 70 | 70 |
| Benzenepentanol, beta-methyl- | 25 | 25 |
| 2.6-octadien-1-ol acetate, 3.7-dimethyl- (2E/Z) | 30 | 30 |
| But-2-en-1-one, 1-(2,6,6-trimethyl-cyclohex-3-enyl)- (E) | 3 | 3 |
| Propyl benzoate | 10 | 10 |
| Methyl dihydrojasmonate (E) | 70 | 70 |
| Amyl salicylate N/Iso | 17 | 17 |
| Benzyl salicylate | 80 | 80 |

-continued

|  | Ref-10 | P10 |
|---|---|---|
| Cis-3 hexenyl salicylate | 10 | 10 |
| Hexyl benzoate, 2-hydroxy- | 33 | 33 |
| 3-Decen-5-ol, 4-methyl- | 5 | 5 |
| Orris Base | 5 | 5 |
| 3-buten-2-one, 3-methyl-4-(2.6.6-trimethyl-2-cyclohexen-1-yl)- | 80 | 80 |
| Benzaldehyde, 3,4-methylendioxy- | 10 | 10 |
| Vanillin | 4 | 4 |
| Cinnamyl alcohol | 4 | 4 |
| 2H-1-benzopyran-2-one | 8 | 8 |
| Acetylcedrene | 70 | 70 |
| Cyclododecane, (ethoxymethoxy)- | 40 | 40 |
| 2-pentanone, 4-cyclohexyl-4-methyl- | 8 | 8 |
| Patchouli Base | 37 | 37 |
| Patchouli oil | 33 | 33 |
| Dioxole, 4H-4a,9-methanoazuleno(5,6-d)-octahydro-2,2,5,8,8,9a-hexamethyl-, 1,3-(Ambrocenide ®), 1.0% in DPG | 20 | 0 |
| Compound of the formula (VIII) 10.0% in DPG |  | 2 |
| Pentadecen-1,15-olide, (11E/Z)- + pentadecen-1,15-olide, 12E- | 40 | 40 |
| Triethyl citrate | 30 | 48 |
| TOTAL | 1000 | 1000 |

The comparative example Ref-10 with Ambrocenide® is a floral Chypre type with an aldehydic top note, paired with floral heart notes and rounded off by patchouli and musk. The replacement of Ambrocenide® by the compound of the formula (VIII) imparts to the whole composition a more nurturing, warmer and more voluminous character; in addition the adhesion is improved.

The perfume oils P1, P2, P3, P4, P5, P6, P7, P8, P9 and P10 from the above perfume oil examples were each separately incorporated into the following formulations.

The olfactory effects described above with each respective perfume oil were in each case also observed in the following formulations.

FORMULATION EXAMPLES

Example F1—Washing Powder

| Material | Chemical Name | Function | Wt. % | Wt. % |
|---|---|---|---|---|
| Sodium metasilicate pentahydrate | sodium metasilicate pentahydrate |  | qsp 100 | qsp 100 |
| Sodium hydrogen carbonate | sodium hydrogen carbonate | alkali | 15.0 | 15.0 |
| Sodium percarbonate | sodium carbonate peroxyhydrate | bleaching agent | 15.0 | 15.0 |
| Peractive AC Blue | TAED/Na carboxymethyl-cellulose | activator | 5.00 | 5.00 |
| Genapol OA-080 | oxo alcohol C14-15, 8EO | nonionic surfactant | 3.00 | 3.00 |
| Texapon K12 Powder | sodium lauryl sulfate C12 | anionic surfactant | 7.00 | 7.00 |
| Tinopal CBS-X |  | brightener | 0.50 | 0.50 |
| Savinase 6.0 T, Type W | protease | enzyme | 0.40 | 0.40 |
| Termamyl 120 T | alpha-amylase | enzyme | 0.30 | 0.30 |
| Sodium sulfate | sodium sulfate | filler | 5.50 | 5.50 |
| Perfume oil P1, P2, P3, P4, P5, P6, P7, P8, P9 or P10 |  | perfume (fragrance) | 0.30 | 0.50 |

Example F2—General Purpose Cleaner

| Material | Chemical Name | Function | Wt. % | Wt. % |
|---|---|---|---|---|
| Deionized water | water | solvent | qsp 100 | qsp 100 |
| Mergal K9N | 5-chloro-2-methyl-3-(2H)-isothiazolone and 2-methyl-3-(2H)-isothiazolone | preservative | 0.1 | 0.1 |
| Trisodium citrate dihydrate | trisodium citrate dihydrate | complexing agent | 3.0 | 3.0 |
| Zetesol NL-2 | fatty alcohol C12-14-sulfate, sodium | anionic surfactant | 30.0 | 30.0 |
| Imbentin C/125/055 | fatty alcohol C12-C15, 8EO | nonionic surfactant | 5.0 | 5.0 |
| Ethanol | ethanol | solvent | 2.0 | 2.0 |
| Perfume oil P1, P2, P3, P4, P5, P6, P7, P8, P9 or P10 |  | perfume (fragrance) | 0.3 | 0.5 |

Example F3—Shampoo

| Material | INCI Name | Wt. % | Wt. % |
|---|---|---|---|
| Deionized water | water | qsp 100 | qsp 100 |
| Plantacare PS 10 | sodium laureth sulfate, lauryl glucoside | 20.0 | 20.0 |
| Euperlan PK 771 | glycol distearate, sodium lauryl sulfate, cocamide MEA, laureth-10 | 6.0 | 6.0 |
| Dragocid Liquid | phenoxyethanol, methylparaben, ethylparaben, butylparaben, propylparaben, isobutylparaben | 0.5 | 0.5 |
| Sodium chloride | sodium chloride | 1.4 | 1.4 |
| Citric acid monohydrate crystalline | citric acid | 0.1 | 0.1 |
| Perfume oil P1, P2, P3, P4, P5, P6, P7, P8, P9 or P10 | perfume (fragrance) | 0.5 | 0.8 |

Example F4—Shower Gel

| Material | INCI Name | Wt. % | Wt. % |
|---|---|---|---|
| Deionized water | water | qsp 100 | qsp 100 |
| Plantacare PS 10 | sodium laureth sulfate, lauryl glucoside | 20.0 | 20.0 |
| Dragocid Liquid | phenoxyethanol, methylparaben, ethylparaben, butylparaben, | 0.5 | 0.5 |

-continued

| Material | INCI Name | Wt. % | Wt. % |
|---|---|---|---|
| Sodium chloride | propylparaben, isobutylparaben sodium chloride | 1.4 | 1.4 |
| Citric acid monohydrate crystalline | citric acid | 1.3 | 1.3 |
| Perfume oil P1, P2, P3, P4, P5, P6, P7, P8, P9 or P10 | perfume (fragrance) | 0.5 | 0.7 |

Example F5—Fabric Conditioner

| Material | Chemical Name | Function | Wt. % | Wt. % |
|---|---|---|---|---|
| Deionized water | water | solvent | qsp 100 | qsp 100 |
| Rewoquat WE 18 | dialkylesterammonium ethosulfate | cationic surfactant | 16.6 | 16.6 |
| Mergal K9N | 5-chloro-2-methyl-3-(2H)-isothiazolone and 2-methyl-3-(2H)-isothiazolone | preservative | 0.10 | 0.10 |
| Dow Corning 1520 Antifoam | polydimethylsiloxane | defoamant | 0.30 | 0.30 |
| Magnesium Chloride 1% solution | magnesium chloride solution | consistency agent | 10.00 | 10.00 |
| Perfume oil P1, P2, P3, P4, P5, P6, P7, P8, P9 or P10 | | fragrance | 0.55 | 0.75 |

Example F6—Eau De Cologne/Eau De Toilette

| Ingredients | Wt. % | Wt. % |
|---|---|---|
| Perfume oil P1, P2, P3, P4, P5, P6, P7, P8, P9 or P10 | 5 | 10 |
| Ethanol | qsp 100 | qsp 100 |
| Water | 18 | 10 |

Example F7—Aerosol Pump Spray

| Ingredients | Wt. % | Wt. % |
|---|---|---|
| Perfume oil P1, P2, P3, P4, P5, P6, P7, P8, P9 or P10 | 1.0 | 1.5 |
| Ethanol | qsp 100 | qsp 100 |
| Water | 5.0 | 8.0 |
| Alpha-tocopherol | 0.20 | 0.20 |
| Hydroxypropylcellulose | 0.20 | — |
| Rosemary extract, soluble in ethanol | 0.22 | — |
| Cetyl alcohol | 1.00 | 0.50 |

Example F8—Shampoo

| Ingredients | Wt. % | Wt. % | Wt. % |
|---|---|---|---|
| Sodium lauryl ether sulfate (e.g. Texapon NSO, Cognis Germany GmbH) | 12 | 12 | 12 |
| Cocamidopropylbetaine (e.g. Dehyton K, Cognis Germany GmbH) | 2 | 2 | 2 |
| Sodium chloride | 1.4 | 1.4 | 1.4 |
| Citric acid | 1.3 | 1.3 | 1.3 |
| Phenoxyethanol, methyl-, ethyl-, butyl- and propylparaben | 0.5 | 0.5 | 0.5 |
| Perfume oil P1, P2, P3, P4, P5, P6, P7, P8, P9 or P10 | 0.3 | 0.5 | 0.7 |
| Water | qsp 100 | qsp 100 | qsp 100 |

Example F9—Detergent Powder

| Ingredients | Wt. % | Wt. % | Wt. % |
|---|---|---|---|
| Linear Na alkylbenzenesulfonate | 8.8 | 8.8 | 8.8 |
| Ethoxylated fatty alcohol C12-18 (7 EO) | 4.7 | 4.7 | 4.7 |
| Na soap | 3.2 | 3.2 | 3.2 |
| Defoamant DOW CORNING(R) 2-4248S POWDERED ANTIFOAM, silicone oil on zeolite as support | 3.9 | 3.9 | 3.9 |
| Zeolite 4A | qsp 100 | qsp 100 | qsp 100 |
| Na carbonate | 11.6 | 11.6 | 11.6 |
| Na salt of a copolymer of acrylic and maleic acid (Sokalan CP5) | 2.4 | 2.4 | 2.4 |
| Na silicate | 3.0 | 3.0 | 3.0 |
| Carboxymethylcellulose | 1.2 | 1.2 | 1.2 |
| Dequest 2066([[(phosphono-methyl)imino]bis[(ethylene-nitrilo)bis(methylene)]]tetrakis-phosphonic acid, sodium salt) | 2.8 | 2.8 | 2.8 |
| Optical brightener | 0.2 | 0.2 | 0.2 |
| Na sulfate | 6.5 | 6.5 | 6.5 |
| Protease | 0.4 | 0.4 | 0.4 |
| Sodium perborate tetrahydrate | 21.7 | 21.7 | 21.7 |
| Perfume oil P1, P2, P3, P4, P5, P6, P7, P8, P9 or P10 | 0.25 | 0.35 | 0.5 |
| EDTA | 1.0 | 1.0 | 1.0 |

Example F10—Liquid Detergent

| Ingredients | Wt. % |
|---|---|
| Deionized water | 39.9 |
| Optical brightener | 0.10 |
| Coco fatty acids (C12-C18) | 7.5 |
| Potassium hydroxide 50% solution | 4.3 |
| Propan-1,2-diol | 5.00 |
| Fatty alcohols C12-C15, 8 EO | 12.0 |
| Na salt of secondary alkylsulfonates (C13-C17) | 17.0 |

| Ingredients | Wt. % |
|---|---|
| Triethanolamine | 2.0 |
| Trisodium citrate dihydrate | 5.0 |
| Dequest 2066([[(phosphono-methyl)imino]bis[(ethylene-nitrilo)bis (methylene)]]tetrakis-phosphonic acid, sodium salt) | 3.0 |
| Ethanol | 3.0 |
| Enzymes | 0.7 |
| Perfume oil P1, P2, P3, P4, P5, P6, P7, P8, P9 or P10 | 0.5 |

Example F11—Liquid Detergent Concentrate

| Ingredients | Wt. % |
|---|---|
| Deionized water | 13.4 |
| Coco fatty acids (C12-C18) | 10.0 |
| Fatty alcohols C12-C15, 8 EO | 26.0 |
| Na salt of secondary alkylsulfonates (C13-C17) | 26.5 |
| Triethanolamine | 8.5 |
| Na salt of fatty alcohol sulfates C12-C14 | 3.0 |
| Ethanol | 5.5 |
| Urea | 4.5 |
| Enzymes | 0.9 |
| Citric acid | 1.0 |
| Perfume oil P1, P2, P3, P4, P5, P6, P7, P8, P9 or P10 | 0.7 |

Application Technology Examples:

Example Intrinsic Adhesion: Compound of the Formula (VIII) Versus Ambrocenide®:

Each fragrance to be tested is dipped as a 10% solution in DPG onto coded scent strips, i.e. the fragrance to be tested is applied onto the scent strip by dipping the respective scent strip into the respective solution of the fragrance to be tested, and odor-assessed directly afterwards at the following time intervals:

1 hour; 3 hours; 10 hours; 1 day; 3 days; 10 days; 1 month; 3 months. The testers assess the odor intensity on a scale from 1=odorless to 9=very strong.

Testing is continued until the mean intensity value from the testers falls below the value of 1.5 (very weak). If 50% of the testers return an intensity of 1, and thus make it clear that the fragrance dipped onto the scent strip is no longer perceived, the test is declared to be ended. In the longest case, testing is continued for 3 months.

| | Compound of the formula (VIII), 10% in DPG | Ambrocenide ®, 10% in DPG |
|---|---|---|
| Intrinsic adhesion | more than 3 months | 10 days |

The compound of the formula (VIII) exhibits markedly longer adhesion on the scent strip than Ambrocenide®.

Example Substantivity on Hair: Compound of the Formula (VIIII) Versus Ambrocenide®:

The fragrance to be tested is incorporated in a quantity of 0.6 wt. % as a 50% solution in DPG into a shampoo formulation analogous to example F8 instead of the perfume oil used there. For each fragrance to be tested, two strands of hair are needed. In addition, as a reference, in each case one pair of hair strands is washed with the unperfumed shampoo formulation of example F8.

All hair strands are washed together with neutral shampoo in a 2 L beaker (min. 2 hrs soaking). Then the hair strands are rinsed well under running water and then dried at room temperature (ca. 23° C.). 100 ml of a 20% aqueous solution is prepared from each shampoo (unperfumed mixture also). Now for each shampoo one strand pair is washed together for 2 mins in the solution. Next, these two strands are rinsed together for 20 secs under flowing, lukewarm water. Both hair strands are combed. One hair strand is wrapped wet in aluminum foil. The second hair strand is dried with a hair dryer.

A tester panel assesses the prepared hair strands by smelling. The testers assess the intensity of the samples on a scale from 0 (odorless) to 6 (very strong).

Order:
a) freshly washed, dry hair
b) freshly washed hair, wet

| Substantivity on hair | Compound of the formula (VIII) | Ambrocenide ® |
|---|---|---|
| Wet hair | 1.4 | 1.2 |
| Dry hair | 1.7 | 0.5 |

The intensity value of the compound of the formula (VIII) on dry hair is higher compared with Ambrocenide® by more than a factor of 3.

Example Substantivity on Cotton: Compound of the Formula (VIII) Versus Ambrocenide®:

The fragrance to be tested is incorporated in a quantity of 0.5 wt. % as a 50% solution in DPG into a fabric softener formulation analogous to example F5 instead of the perfume oil used there.

Cotton cloths are washed neutral at 95° C. in a washing machine and dried in air at room temperature.

In each case, two identically coded cotton cloths are rinsed with 370 g of a 1% aqueous fabric softener liquor containing the respective fragrance to be tested in a pot of the Linitest machine in the fabric softener program. Next, the liquor is poured out of the individual pots, the cloths wrung pot by pot, and all cloth pairs spin-dried as a pair for 20 secs. Then one cloth from each cloth pair is shrink-wrapped wet, and one hung out to dry.

A test panel assesses the prepared samples by smelling.

The testers assess the intensity of the samples on a scale from 0 (odorless) to 6 (very strong)

In each case they start with the unperfumed specimen and then the samples.

Order:
a) dry laundry
b) wet laundry

| Substantivity on cotton | Compound of the formula (VIII) | Ambrocenide ® |
|---|---|---|
| Wet laundry | 1.6 | 1.2 |
| Dry laundry | 1.5 | 0.8 |

The intensity value of the compound of the formula (VIII) on dry laundry is higher by a factor of 2 compared with Ambrocenide®, and even the intensity of wet laundry is assessed higher for the compound of the formula (VIII).

In addition, the dry cotton cloths were stored over a longer period and each assessed as described above after several days.

| Day 3 | Compound of the formula (VIII) | 2.00 |
| | Ambrocenide ® | 1.20 |
| Day 8 | Compound of the formula (VIII) | 1.79 |
| | Ambrocenide ® | 0.93 |
| Day 10 | Compound of the formula (VIII) | 1.80 |
| | Ambrocenide ® | 1.10 |
| Day 14 | Compound of the formula (VIII) | 1.69 |
| | Ambrocenide ® | 0.92 |
| Day 18 | Compound of the formula (VIII) | 1.80 |
| | Ambrocenide ® | 0.50 |

The intensity of the compound of the formula (VIII) even after a period of 18 days is still assessed as markedly stronger compared with Ambrocenide®.

The invention claimed is:

1. A compound of the formula (II) or (II')

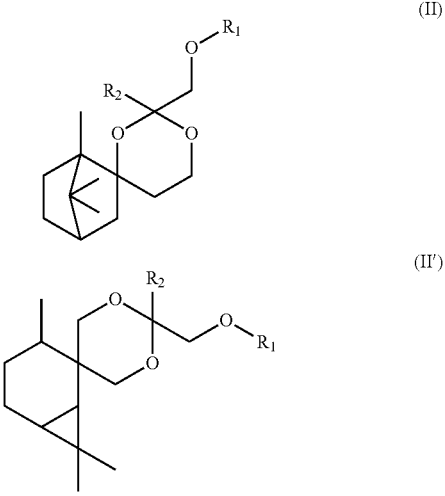

wherein $R_1$ is hydrogen or $C_1$-$C_3$ alkyl, and $R_2$ is hydrogen or $C_1$-$C_4$ alkyl, or (b) according to the formula (III)

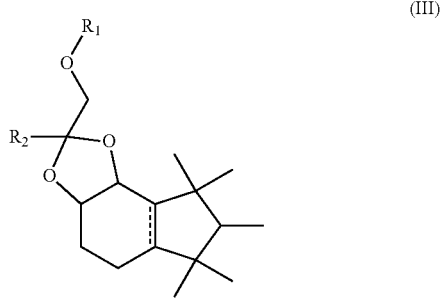

wherein $R_1$ is hydrogen or $C_1$-$C_3$ alkyl, and $R_2$ hydrogen or $C_1$-$C_4$ alkyl and the compound is saturated or unsaturated, or (c) according to formula (IV) or (IV')

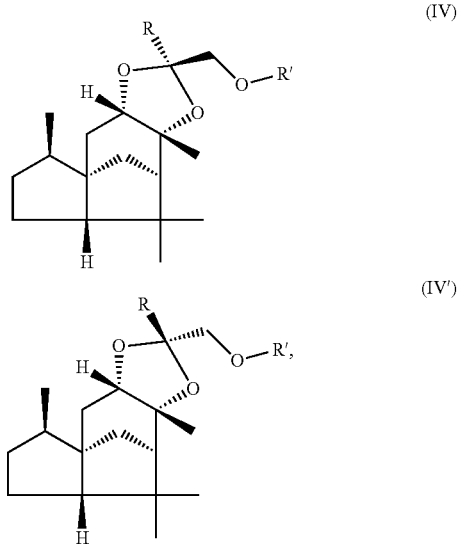

wherein R=H or $C_1$-$C_4$ alkyl and R'=H or $C_1$-$C_3$ alkyl.

2. A composition comprising
   (i) one or more 3,6,8,8-tetramethyl-octahydro-3a,7-methano-azulen-5,6-diol ketal(s) and
   (ii) one or more compound(s) of the formulae (II), (II'), (III), (IV) and/or (IV') according to claim 1, wherein the total content of the compounds of the formulae (II), (II'), (III), (IV) and/or (IV') is greater than 40 wt. %, based on the total amount of 3,6,8,8-tetramethyl-octahydro-3a,7-methano-azulen-5,6-diol ketal(s) contained in the composition, and/or
   wherein
   the weight ratio of compound(s) of the formula (IV) to compound(s) of the formula (IV'), if present, lies in the range from 4:1 to 1:10.

3. A fragrance mixture, comprising a composition according to claim 2, as well as one or more (further) compound(s) not corresponding to the fragrances of the formulae (II), (III), (IV), or (IV'), wherein
   (i) the quantity of the compound(s) of the formulae (II), (II'), (III), (IV), or (IV'), is sufficient to mediate an ambergris and/or wood fragrance note, and/or
   (ii) the (further) fragrances not corresponding to the formulae (II), (II'), (III), (IV), or (IV'), mediate one, several or all of the notes fruity, floral, spicy, woody, musk and ambrette and the quantity of the compound(s) of the formula (II), (II'), (III), (IV), or (IV'), is sufficient to modify and/or to intensify one, several or all of the notes fruity, floral, spicy, woody, musk and ambrette, and/or
   (iii) the quantity of the compound(s) of the formulae (II), (II'), (III), (IV), or (IV'), is sufficient to impart to the fragrance mixture an impression of volume, complexity, elegance and/or naturalness, and/or
   (iv) the quantity of the compound(s) of the formulae (II), (II'), (III), (IV), or (IV'), is sufficient, in comparison to an otherwise identically constituted fragrance mixture without compounds of the formulae (II), (II'), (III), (IV), or (IV'), to create a more nurturing, more harmonious, higher quality and/or more natural olfactory impression.

4. A method for intensifying an odor or several odors selected from the group consisting of fruity, floral, spicy, woody, musk and ambrette, comprising the following step:
  (i) providing one or more fragrance(s) with one, several or all of the notes selected from the group consisting of fruity, floral, spicy, woody, musk and ambrette, and
  (ii) mixing said one or more fragrance(s) with
    (ii-ii) the composition according to claim 2 in a quantity which suffices to intensify the olfactory impression of the fragrance(s).

5. A perfumed product containing a composition, according to claim 2, in a sensorily effective quantity, wherein the product contains one or more surfactants.

6. A method for intensifying an odor, comprising incorporating a compound as claimed in claim 1 into a fragrance or fragrance mixture,
  means for increasing substantivity and/or retention of a fragrance mixture, or fixative.

7. A fragrance mixture, comprising
  one or more compound(s) of the formulae (II), (II'), (III), (IV) and/or (IV') according to claim 1, as well as
  one or more (further) compound(s) not corresponding to the fragrances of the formulae (II), (II'), (III), (IV) or (IV'), wherein
  (i) the quantity of the compound(s) of the formulae (II), (II'), (III), (IV) or (IV'), is sufficient to mediate an ambergris and/or wood fragrance note, and/or
  (ii) the (further) fragrances not corresponding to the formulae (II), (II'), (III), (IV), or (IV'), mediate one, several or all of the notes fruity, floral, spicy, woody, musk and ambrette and the quantity of the compound(s) of the formula (II), (II'), (III), (IV), or (IV'), is sufficient to modify and/or to intensify one, several or all of the notes fruity, floral, spicy, woody, musk and ambrette, and/or
  (iii) the quantity of the compound(s) of the formulae (II), (II'), (III), (IV), or (IV'), is sufficient to impart to the fragrance mixture an impression of volume, complexity, elegance and/or naturalness, and/or
  (iv) the quantity of the compound(s) of the formulae (II), (II'), (III), (IV), or (IV'), is sufficient, in comparison to an otherwise identically constituted fragrance mixture without compounds of the formulae (II), (II'), (III), (IV), or (IV'), to create a more nurturing, more harmonious, higher quality and/or more natural olfactory impression.

8. The fragrance mixture, of claim 7, wherein the quantity of the compound(s) of the formulae (II), (II'), (III), (IV), or (IV'), lies in the range from 0.0001 to 25 wt. %, based on the total weight of the fragrance mixture.

9. The fragrance mixture of claim 7, further containing
  (i) one or more wood and/or ambergris fragrance(s) not corresponding to the formulae (II), (II'), (III), (IV), or (IV'), and/or
  (ii) one or more musk fragrance(s).

10. The fragrance mixture of claim 9, wherein the musk fragrance(s) is/are selected from the group consisting of macrocyclic musk fragrances, nitro musk fragrances, polycyclic musk fragrances, alicyclic musk fragrances and mixtures thereof.

11. The fragrance mixture of claim 9, wherein the weight ratio of musk fragrances to the compound(s) of the formulae (II), (II'), (III), (IV) or (IV'), lies in the range from 100:1 to 100,000:1.

12. A method for endowing hair or textile fibers with one, several or all of the notes selected from the group consisting of fruity, floral, spicy, woody, musk and ambrette, comprising the following steps:
  (i) preparing a fragrance mixture according to claim 7, wherein the (further) fragrance(s) not corresponding to the formulae (II), (II'), (III), (IV), or (IV'), mediate(s) one, several or all of the notes fruity, floral, spicy, woody, musk and ambrette and the quantity of the compound(s) of the formulae (II), (II'), (III), (IV), or (IV'), is sufficient to modify and/or to intensify one, several or all of the notes fruity, floral, spicy, woody, musk and ambrette, and
  (ii) applying the fragrance mixture onto the hair or the textile fibers.

13. A method for intensifying an odor or several odors selected from the group consisting of fruity, floral, spicy, woody, musk and ambrette, comprising the following step:
  (i) providing one or more fragrance(s) with one, several or all of the notes selected from the group consisting of fruity, floral, spicy, woody, musk and ambrette, and
  (ii) mixing said one or more fragrance(s) with
    (ii-iii) the fragrance mixture of claim 7 in a quantity which suffices to intensify the olfactory impression of the fragrance(s).

14. A perfumed product containing a fragrance mixture, according to claim 7, in a sensorily effective quantity, wherein the product contains one or more surfactants.

15. A method for intensifying an odor or several odors selected from the group consisting of fruity, floral, spicy, woody, musk and ambrette, comprising the following step:
  (i) providing one or more fragrance(s) with one, several or all of the notes selected from the group consisting of fruity, floral, spicy, woody, musk and ambrette, and
  (ii) mixing said one or more fragrance(s) with
    (ii-i) one or more compound(s) of the formula (II), (II'), (III), (IV), or (IV'), of claim 1, in a quantity which suffices to intensify the olfactory impression of the fragrance(s).

16. A perfumed product containing one or more compound(s) of the formulae (II), (II'), (III), (IV), or (IV'), according to claim 1, in a sensorily effective quantity, wherein the product contains one or more surfactants.

17. The perfumed product of claim 16, selected from the group consisting of detergents, cleaners, sanitary agents and toiletries, in particular for use in the field of body care, hair care, cosmetics or the household.

* * * * *